United States Patent
Pradhan et al.

(10) Patent No.: US 9,963,705 B2
(45) Date of Patent: May 8, 2018

(54) DNMT INHIBITORS

(71) Applicant: New England Biolabs, Inc., Ipswich, MA (US)

(72) Inventors: Sriharsa Pradhan, Wenham, MA (US); Pierre O. Esteve, Beverly, MA (US); Guoqiang Zhang, Reading, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days. days.

(21) Appl. No.: 15/034,092

(22) PCT Filed: Nov. 10, 2014

(86) PCT No.: PCT/US2014/064779
§ 371 (c)(1),
(2) Date: May 3, 2016

(87) PCT Pub. No.: WO2015/073360
PCT Pub. Date: May 21, 2015

(65) Prior Publication Data
US 2016/0272977 A1    Sep. 22, 2016

Related U.S. Application Data

(60) Provisional application No. 61/903,004, filed on Nov. 12, 2013.

(51) Int. Cl.
*C12N 15/113* (2010.01)
*A61K 31/7105* (2006.01)

(52) U.S. Cl.
CPC ...... *C12N 15/1137* (2013.01); *A61K 31/7105* (2013.01); *C12Y 201/01037* (2013.01); *C12N 2310/11* (2013.01); *C12N 2310/141* (2013.01); *C12N 2310/151* (2013.01); *C12N 2320/30* (2013.01)

(58) Field of Classification Search
CPC .................................................. C12N 15/113
See application file for complete search history.

(56) References Cited

U.S. PATENT DOCUMENTS

| | | | | |
|---|---|---|---|---|
| 7,300,922 B2* | 11/2007 | Sullenger | ............. | C12N 15/113 435/320.1 |
| 2003/0083292 A1* | 5/2003 | MacLeod | ........... | C12N 15/1137 514/44 A |
| 2008/0132525 A1* | 6/2008 | Wahhab | ............... | C07D 471/04 514/263.4 |
| 2009/0083873 A1* | 3/2009 | Hutvagner | ............ | C12N 15/111 800/21 |
| 2013/0165502 A1* | 6/2013 | Marsh | ................ | A61K 31/7088 514/44 R |
| 2015/0315628 A1* | 11/2015 | Shen | ..................... | C12Q 1/6897 435/6.12 |

FOREIGN PATENT DOCUMENTS

| WO | WO2010012667 | 2/2010 |
|---|---|---|
| WO | WO2012142480 | 10/2012 |

OTHER PUBLICATIONS

Cree et al. FEBS Letters 590 (2016) 2870-2883.*
Dhe-Paganon et al. Int. J. Biochem Mol. Biol 2011:58-66.*
Okano et al. Cell 99: 247-257, 1999.*
Thiel, et al., Nucleic Acid Therapeutics, 21, 4, 253-263, 2011.
Song, et al., Science, 331(6020):1036-1040, 2011.
Tsankova, et al., Nat. Rev. Neurosci. 8:355-67, 2007.
Weaver, et al., Nat. Neurosci. 7:847-54, 2004.
Pradhan, et al., EMBO J. 21(4): 779-88, 2002.
Pradhan, et al., J. Biol. Chem. 274(46):33002-33010, 1999.
Bacolla, et al., J.Biol. Chem., 274:33011-33019, 1999.
Muller, et al., Nature Chem., 2:1095-1098, 2010.
Paeschke, et al., Nature Structural & Mol. Biol., 12(10):847-854, 2005.
Deplus, et al., Cell Reports, 8, 743-453, 2014.

* cited by examiner

*Primary Examiner* — Brian A Whiteman
(74) *Attorney, Agent, or Firm* — New England Biolabs, Inc; Harriet M. Strimpel

(57) ABSTRACT

RNA molecules inhibiting a DNMT and methods and compositions incorporating or generating the RNA molecules are described.

5 Claims, 15 Drawing Sheets

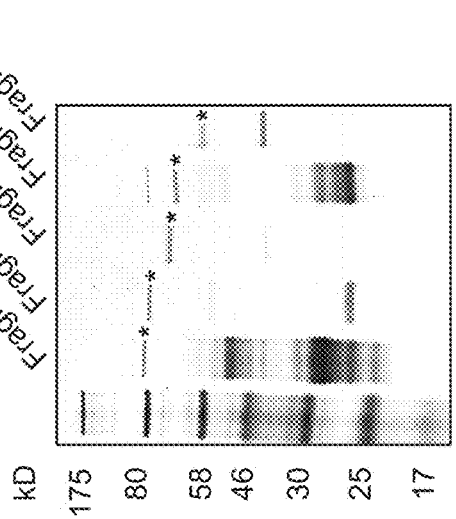
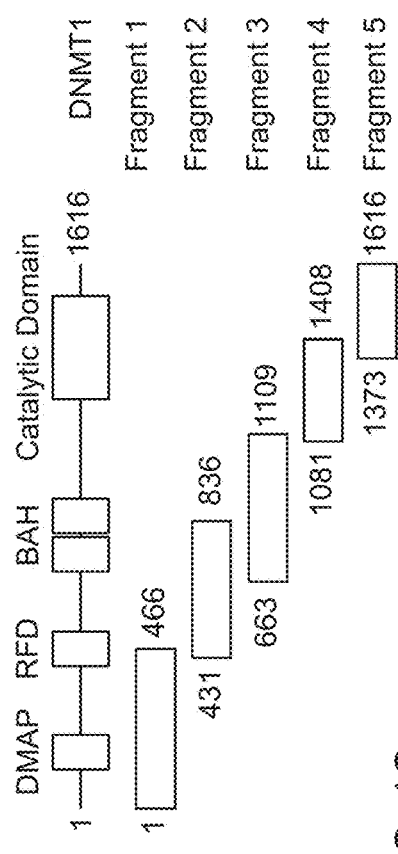
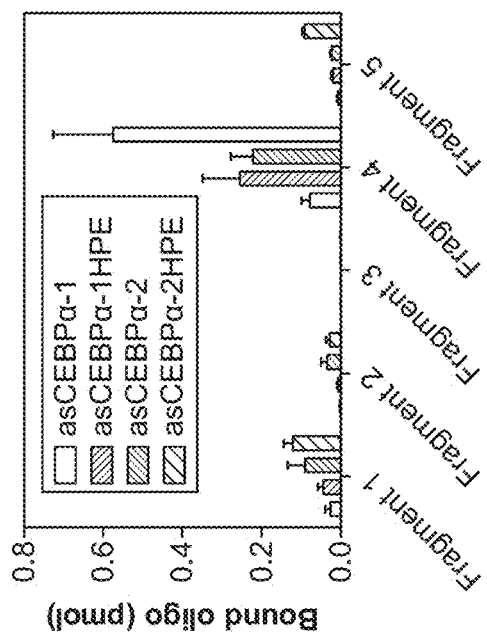
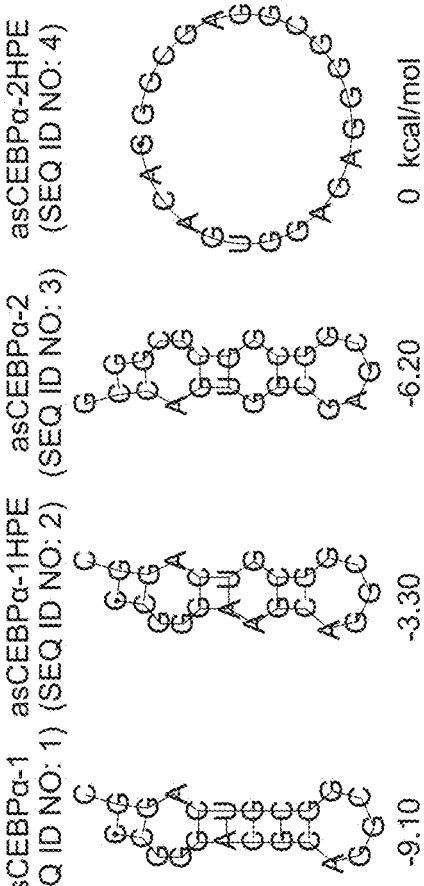
FIG. 1A
FIG. 1B
FIG. 1C
FIG. 1D

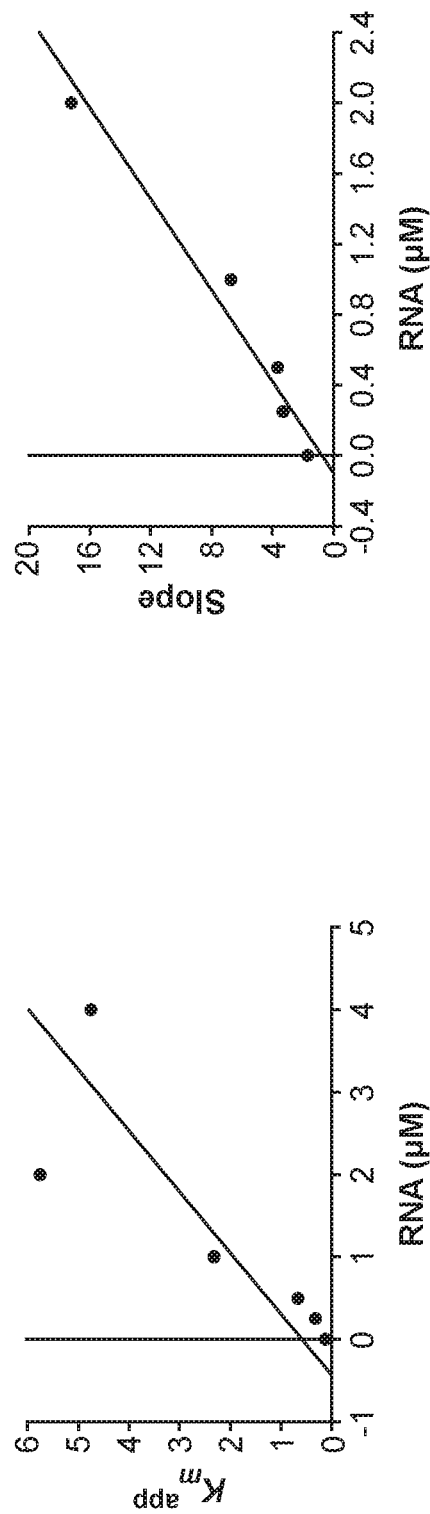

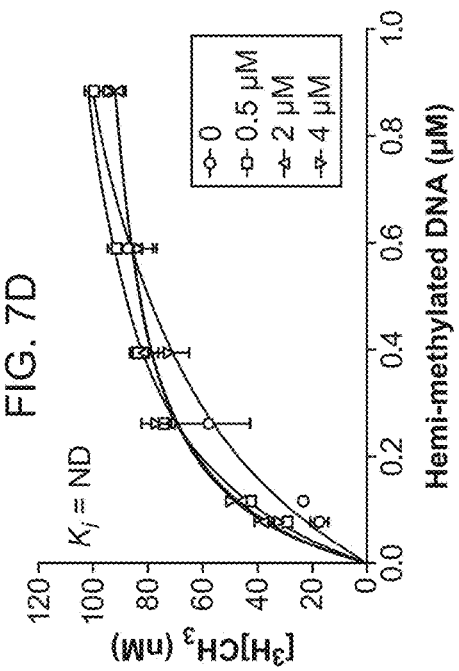
FIG. 7B
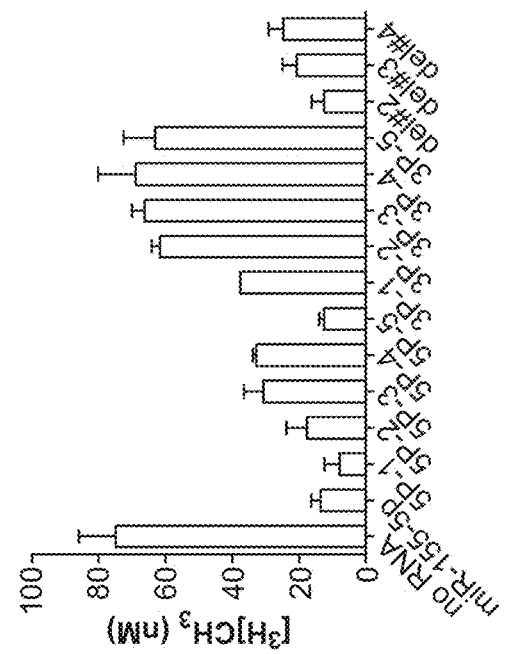
FIG. 7A
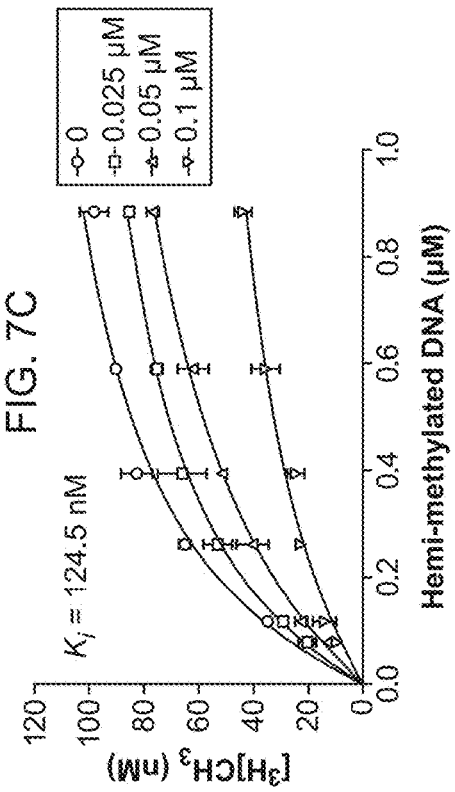
FIG. 7D
FIG. 7C

FIG. 10A
FIG. 10B
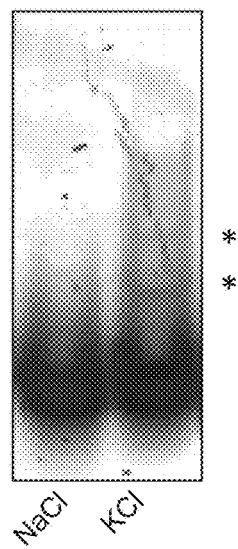
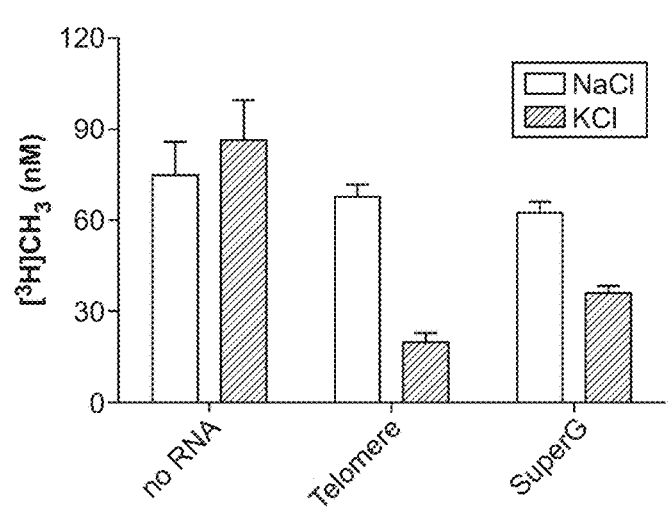
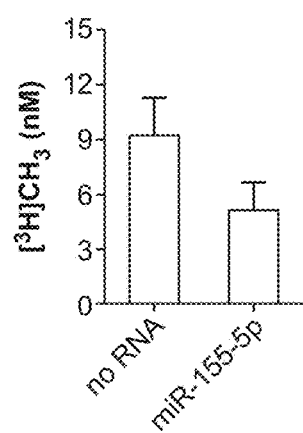
FIG. 11

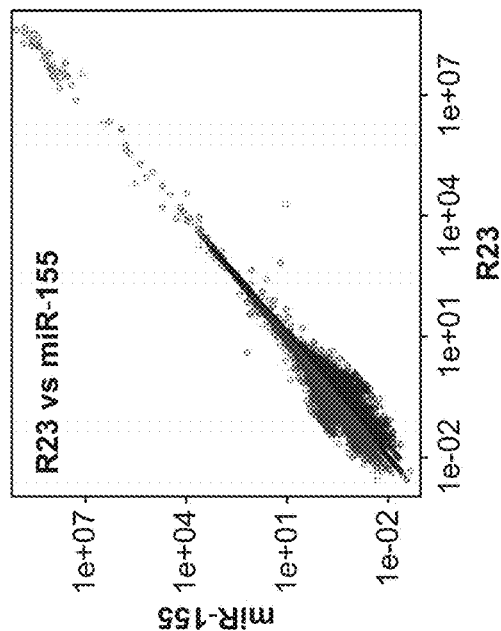
FIG. 17
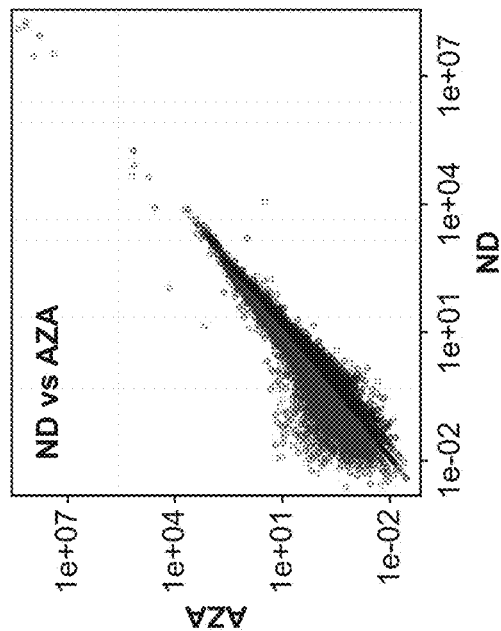
FIG. 18
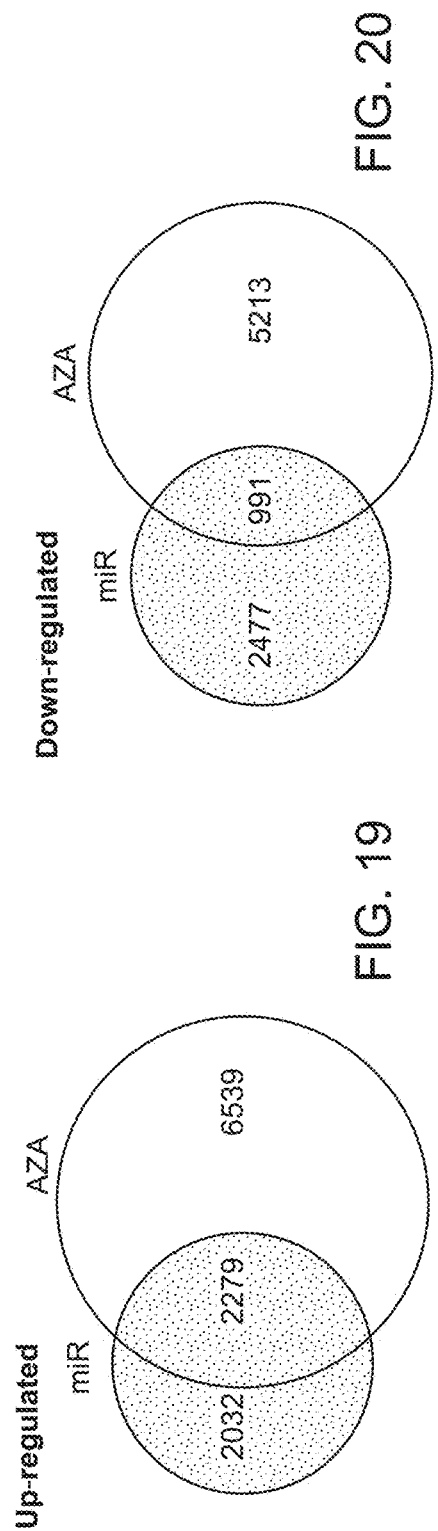
FIG. 19
FIG. 20

DNMT INHIBITORS

CROSS REFERENCE

This application is a § 371 application of International Application No. PCT/US2014/064779 filed Nov. 10, 2014, which claims priority from U.S. Provisional Application No. 61/903,004, filed Nov. 12, 2013, herein incorporated by reference.

BACKGROUND OF THE INVENTION

Maintenance DNA methylation in mammalian genome is required for transcriptional gene silencing, X chromosome inactivation and heterochromatin formation. The mammalian maintenance DNA (cytosine-5) methyltransferase 1 (DNMT1) contains several domains, including a domain targeting replication foci, a DNA-binding "CXXC" domain, a pair of "bromo-adjacent homology" or "BAH" domains, and a C-terminal catalytic domain that shares homology with most bacterial cytosine-5 methyltransferases. DNMT1 plays a significant role during development, and is required for embryonic survival in mice. DNMT1 adds methyl groups to hemimethylated DNA during DNA replication. Other DNA methyltransferases in mammals include DNMT-3A and 3B.

In human cancer, the DNA methylation pattern becomes aberrant, resulting in hypermethylation and transcriptional silencing of the promoters of a number of tumor suppressor genes. Restoring the expression of hypermethylated tumor suppressor genes by inhibiting the DNA methyltransferases (DNMT1, DNMT3A, and DNMT3B) has emerged as a desirable strategy against cancer. DNMT1 is more highly expressed when cells are replicating their DNA, and is therefore a promising target for inhibiting methylation in rapidly dividing cells such as cancer cells. The DNA methyltransferase (DNMT) inhibitors azacytidine and decitabine are the most successful epigenetic drugs to date for clinical use in mixed-lineage leukemia ("MLL"), myelodysplastic syndrome ("MDS") and acute myelogenous leukemia ("AML") patients, and are still the most widely used as epigenetic modulators, even though their application is restricted by their relative toxicity and poor chemical stability in vivo. Zebularine (1-(β-D-ribofuranosyl)-1,2-dihydropyrimidin-2-one), a more stable cytidine analog, is another inhibitor of DNMT with concomitant inhibitory activity towards cytidine deaminase. Although many new inhibitors of DNMT have been identified, none of them can so far replace azacytidine, decitabine and, to a lesser degree, zebularine.

SUMMARY OF THE INVENTION

The methods and compositions described herein are based, in part, on the identification of specific small RNA molecules or their derivatives involved in inhibiting mammalian DNA methyltransferases. In one embodiment, a method for inhibiting a mammalian (e.g. human) DNMT such as DNMT1 or DNMT3, or a protein comprising a sequence at least 80%, at least 85%, at least 90%, at least 95%, or at least 99% identical to one of these DNMTs is provided. DNMT activity can be inhibited globally (in a manner that is not targeted to a single target gene, for example) by exposing the DNMT to an RNA at a concentration sufficient to inhibit DNMT activity on DNA, such as on human DNA. This can be used to restore a desired pattern of DNA methylation in a mammalian (e.g. human) subject, such as a human or other mammalian cell or a person. In the methods described herein, at least one of the following conditions is met (and, optionally, at least two, at least three, at least four, at least five, at least six, or all seven conditions are simultaneously met): (a) the RNA is not present as a complex with an extra-coding RNA (i.e., a transcribed pre-mRNA including both coding and non-coding regions or only non-coding regions) of a human gene; (b) the RNA is single-stranded; (c) if the DNA is a human gene, the RNA is not at least 80% complementary to the DNA of the human gene; (d) the inhibition of DNMT activity is global/not target-specific; (e) the RNA is no more than 13 nucleotides in length (defined further herein); (f) the RNA has an inhibitory constant (Ki) for the DNMT of no more than 10 uM, (defined further herein); and/or (g) the RNA has a 5' end and a 3' end and at least two of the five nucleotides closest to the 3' end are guanine.

The DNMT may be exposed to the RNA in vitro or in vivo. In some embodiments, the DNMT is exposed to the RNA by administration of the RNA to a cell or an organism. In other embodiments, the DNMT is exposed to the RNA by administration of an expression vector encoding the RNA. The expression vector includes a promoter which drives synthesis of the RNA in a cell.

In embodiments methods are provided for treating a disease or disorder associated with dysregulated methylation by inhibiting the DNMT (e.g. DNMT1), by any of the methods described herein, in a patient (e.g. a human, or a mammalian veterinary patient) having the disease or disorder. In various embodiments, the disease or disorder is a cancer, such as a leukemia, a lymphoma, or a solid tumor, and can be, for example, renal cell carcinoma (RCC), colorectal cancer, AML, chronic myelogenous leukemia (CML), MLL or glioma. In another embodiment, the disease or disorder is a MDS, Alzheimer's disease, autism, bipolar disorder, schizophrenia, asthma, kidney disease, glaucoma, or muscular dystrophy.

Synthetic RNA molecules useful for inhibiting a DNMT (e.g. DNMT1) are also described herein. In certain embodiments, the synthetic RNA is non-naturally occurring. For example, one or more of the linkages between nucleotides may be replaced with a phosphorothioate linkage or other non-phosphodiester linkage to enhance stability. Similarly, one or more modified nucleotides can be incorporated, such as a fluoro-, amino- or O-methyl-2'-ribose-modified nucleotide.

Embodiments of the compositions include for example, an in vitro preparation of a DNMT (e.g. DNMT1) and an RNA inhibitor of the DNMT. The RNA inhibitor inhibits the activity of the DNMT on DNA, such as human DNA. These compositions can be prepared by, for example, introducing an exogenous RNA inhibitor into a cell containing the DNMT, and isolating a preparation (e.g. a lysate) containing the DNMT and the RNA inhibitor, which may be bound together; introducing an exogenous DNMT into a cell containing the RNA inhibitor, and isolating a preparation containing the DNMT and the RNA inhibitor; or admixing a DNMT and an RNA inhibitor in vitro.

Pharmaceutical compositions containing a pharmaceutically acceptable carrier and either an RNA or a nucleic acid complementary to the RNA or to its complement is also described herein. The nucleic acid complementary to the RNA or to its complement can be an RNA, a DNA, or an analog thereof and can be, for example, an expression vector encoding the RNA and capable of driving its expression in a human cell. In certain embodiments, the RNA is no more than 30 nucleotides in length and meets at least one (or at least two, or at least three, or all four) of the following conditions: (a) the RNA has a 5' end and a 3' end, wherein at least two of the five nucleotides closest to the 3' end contain guanine; (b) the RNA has an inhibitory constant ($K_i$) for DNMT of no more than 400 nM; (c) the RNA is no more than 13 nucleotides in length and has an inhibitory constant ($K_i$) for DNMT of no more than 600 nM; and/or (d) the RNA is not at least 80% complementary to any human extra-coding RNA and has an inhibitory constant ($K_i$) for DNMT of no more than 10 µM.

The methods and compositions described herein use an RNA that binds to a DNMT protein, and may be able to bind a fragment of DNMT (e.g. DNMT1) containing most or all of the catalytic domain and the preceding GK linker region (rich in glycine and lysine residues), such as a fragment containing amino acids 1081-1408 of human DNMT1. In some embodiments, the RNA may have an inhibitory constant ($K_i$) for a DNMT (such as DNMT1) of no more than 10 µM; no more than 5 µM, no more than 4 µM; no more than 3 µM; no more than 2 µM; no more than 1 µM; no more than 600 nM; no more than 500 nM; no more than 400 nM; no more than 300 nM; no more than 200 nM; no more than 100 nM; no more than 90 nM; no more than 80 nM; no more than 70 nM; no more than 60 nM; no more than 50 nM; no more than 40 nM; or no more than 30 nM. The RNA does not need to be more than 30 nucleotides in length, and indeed may be substantially shorter, such as no more than 20 nucleotides in length, no more than 15 nucleotides in length, no more than 14 nucleotides in length; no more than 13 nucleotides in length; no more than 12 nucleotides in length; no more than 11 nucleotides in length; no more than 10 nucleotides in length; no more than 9 nucleotides in length; no more than 8 nucleotides in length; no more than 7 nucleotides in length; or no more than 6 nucleotides in length. In certain embodiments, the RNA is at least 4, at least 5, at least 6, at least 7, at least 8, at least 9, at least 10, at least 11, or at least 12 nucleotides in length.

The RNA used in the methods and compositions typically has a uniform sequence, rather than being a mixture of different RNAs having varying sequences. In certain embodiments, at least two, at least three or at least four of the last five nucleotides of the RNA contain a guanine base or a derivative of a guanine base. Optionally, the at least two, at least three, or at least four nucleotides containing a guanine base (or derivative thereof) may not include the final nucleotide at the 3' end of the RNA. For example, if the RNA contains N nucleotides, counting the last five nucleotides of the RNA from the 5' end toward the 3' end, then the RNA may optionally contain a guanine base (or derivative thereof) at positions N-5 and N-4; N-5 and N-3; N-5 and N-2; N-4 and N-3; N-4 and N-2; N-3 and N-2; N-5, N-4 and N-3; N-5, N-4 and N-2; N-5, N-3 and N-2; N-4, N-3 and N-2; or N-5, N-4, N-3 and N-2. Although a uniform sequence is described above, a mixture of different RNAs having varying sequences may be used where the characteristics of the different RNAs conform with the above description.

In some embodiments, the RNA does not form secondary structures that reduce its free energy by more than 4 kcal/mol. In other embodiments, the RNA is present as a G-quadruplex in which 4 guanine bases associate to create a four-stranded structure also known as a G-tetrad.

The RNA may comprise, consist essentially of, or consist of a nucleotide sequence having at least 80%, at least 85%, at least 90%, at least 95%, or at least 99% sequence identity to a nucleotide sequence selected from any one of SEQ ID NOs: 1-20 or 22-39. In particular embodiments, the RNA comprises, consists essentially of, or consists of a nucleotide sequence selected from any one of SEQ ID NOs: 1-20 or 22-39. In particular embodiments, the RNA comprises, consists essentially of, or consists of a nucleotide sequence having at least 80%, at least 85%, at least 90%, at least 95%, or at least 99% sequence identity to a nucleotide sequence selected from SEQ ID NO: 4, SEQ ID NO: 5, and SEQ ID NO: 23; such as a nucleotide sequence selected from any one of SEQ ID NOs: 4, 5 or 23. In particular embodiments, the RNA comprises, consists essentially of, or consists of a nucleotide sequence having at least 80%, at least 85%, at least 90%, at least 95%, or at least 99% sequence identity to a nucleotide sequence selected from any of SEQ ID NOs: 35-39; such as a nucleotide sequence selected from any one of SEQ ID NOs: 35-39. In particular embodiments, the RNA comprises, consists essentially of, or consists of the consensus nucleotide sequence SEQ ID NO: 40.

The RNA may resemble a natural nucleic acid or it may contain one or more modifications.

In certain embodiments, the RNA is present in a pharmaceutical composition with a pharmaceutically acceptable carrier. The RNA may optionally be present in a vehicle, such as a liposome, facilitating penetration of the RNA into cells following administration of the composition. The RNA can be present within a viral vector, such as a virus capable of replication, or a nonreplicating virus, such as one or more viral proteins (e.g. capsid proteins) housing the RNA inhibiting the DNMT and potentially including little or no viral RNA. Suitable viral vectors can be derived from a DNA virus, a single-stranded RNA virus, or a double-stranded RNA virus. Viral vectors typically include at least an envelope protein in which the inhibitory RNA (or DNA encoding it) is packaged, and may include little or no viral nucleic acid. In certain embodiments, the composition also includes an inhibitor of a ribonuclease, an enzyme that cuts RNA molecules.

In various embodiments, the methods and compositions described herein are used to restore expression of methylation-silenced tumor suppressor genes in a subject (e.g. a cell or an organism); to increase expression of a tumor suppressor gene in a subject; to inhibit tumorigenicity in vitro or in vivo in a subject; to inhibit cell growth; to induce apoptosis; to reduce global DNA methylation; to reprogram the epigenetics of a cell; to achieve DNA hypomethylation in combination with administration of a nucleoside analog such as azacytidine, decitabine, or zebularine.

Various advantages of embodiments will become apparent to those skilled in the art from the following detailed description of the preferred embodiments, when read in light of the accompanying drawings.

BRIEF DESCRIPTION OF THE FIGURES

FIG. 1A provides a schematic depiction of the domain structure of human DNMT1 and describes five GST-DNMT1 fragment fusion proteins (fragments 1-5). The domains of DNMT1 recited in FIG. 1A include "DMAP" (DNA methyltransferase associated protein binding domain), "RFD" (replication foci domain), BAH, and the catalytic domain. A "GK linker," not shown, is present between the BAH domain and the catalytic domain. FIG. 1B, is an image of a quantitative SDS polyacrylamide gel electrophoresis of GST-DNMT1 fragment fusion proteins used in RNA-DNMT1 fragment binding assays. Corresponding protein bands of the GST-DNMT1 fragments are marked by asterisks. FIG. 1C, is a bar graph depicting the results of a GST pull-down assay showing the preferential binding of folded RNA oligo asCEBPα-1 (antisenseCEBPα-1), asCEBPα-1HPE (antisenseCEBPα-1 high positionalentropy), asCEBPα-2 (antisenseCEBPα-2) and asCEBPα-2HPE (antisenseCEBPα-2 high positional entropy) to DNMT1 fragment 4 in a free energy-dependent manner. FIG. 1D provides schematic depictions of the secondary structures of the RNA oligos used in the GST pull-down assay, including asCEBPα-1 (SEQ ID NO:1), asCEBPα-1HPE (SEQ ID NO:2), asCEBPα-2 (SEQ ID NO:3), and asCEBPα-2HPE (SEQ ID NO:4). Beneath each structure is the free energy of the folded RNA.

FIG. 2A-2F provides graphs showing schematic depictions of the inhibitory activity of asCEBPα-2 on DNMT1 compared with hemi-methylated DNA and AdoMet substrates. FIGS. 2A and 2B depict representative initial velocity curves of full-length DNMT1 activity in the presence of variable concentrations of asCEBPα-2. The concentrations of [$^3$H]CH$_3$ incorporated into hemimethylated DNA by 20 nM of DNMT1 per 30 minutes were plotted against variable hemimethylated DNA (FIG. 2A) or AdoMet (S-adenosyl methionine) concentrations (FIG. 2B). FIGS. 2C and 2D are double reciprocal plots of FIGS. 2A and 2B for fixed asCEBPα-2 concentration. The position where the plots intersect indicates that asCEBPα-2 competitively inhibits DNMT1 activity versus a hemimethylated DNA substrate (FIG. 2C) while the inhibition pattern against AdoMet is mixed (FIG. 2D). FIG. 2E is a representative figure depicting the deduction of $K_i$ in asCEBPα-2 versus hemimethylated DNA competitive inhibition studies. $K_m^{app}$ is obtained from the nonlinear regression of curves in FIG. 2A. FIG. 2F is a representative figure depicting the deduction of $K_i$ in asCEBPα-2 versus AdoMet mixed inhibition studies. The y axis values, slopes, are the slopes of the double reciprocal plots in FIG. 2D.

FIG. 3A is a bar graph depicting the concentration of [$^3$H]CH$_3$ incorporated by 10 nM DNMT1 into 1 μM of hemimethylated DNA substrate in 15 minutes in the presence of 5.28 μM of RNA oligonucleotides. FIG. 3B is a bar graph depicting the concentration of [$^3$H]CH$_3$ incorporated into 2 ng/μL of pUC19 DNA substrate in 30 minutes in the presence of 5 μM of miR-155-5p. M.SssI was used at 0.08 U/μL, M.HhaI was used at 0.5 U/μL and M.HpaII was used at 0.08 U/μL, respectively.

FIGS. 4A and 4B provide schematic depictions of the initial velocity curve of full-length DNMT1 activity in the presence of variable concentrations of miR-17-5p. The concentrations of [$^3$H]CH$_3$ incorporated into hemimethylated DNA by 20 nM of DNMT1 per 30 minutes were plotted against variable hemimethylated DNA (FIG. 4A) or AdoMet concentrations (FIG. 4B). FIGS. 4C and 4D depict double reciprocal plots of FIGS. 4A and 4B for fixed miR-17-5p concentration. The position where the plots intersect indicates that miR-17-5p competitively inhibits DNMT1 activity versus hemimethylated DNA substrate (FIG. 4C) while the inhibition pattern against AdoMet is mixed (FIG. 4D).

FIG. 5A is a schematic depiction of an initial velocity curve of 20 nM of DNMT1 in the presence of 0, 0.0125, 0.025, 0.03333 and 0.05 μM of miR-155-5p oligo. FIG. 5B depicts double reciprocal plots of FIG. 5A showing the competitive inhibition pattern of miR-155-5p versus hemimethylated DNA substrate. FIG. 5C depicts the determination of $K_i$ in a representative miR-155-5p versus hemimethylated DNA competitive inhibition study. $K_m^{app}$ is obtained by nonlinear regression of curves in FIG. 5A.

FIG. 7A-7D shows that small RNA subspecies (smaller than miRNAs) are potent DNMT1 inhibitor in a competitive manner. FIG. 7A depicts the sequences of miR-155-5p (SEQ ID NO:5) and of a series of deletions truncating the 5' or 3' end or deleting internal nucleotides (5p-1, SEQ ID NO:6; 5p-2, SEQ ID NO:7; 5p-3, SEQ ID NO:8; 5p-4, SEQ ID NO:9; 5p-5, SEQ ID NO:10; 3p-1, SEQ ID NO:11; 3p-2, SEQ ID NO:12; 3p-3, SEQ ID NO:13; 3p-4, SEQ ID NO:14; 3p-5, SEQ ID NO:15, del#2, SEQ ID NO:16, del#3, SEQ ID NO:17; del#4, SEQ ID NO:18). In each case deleted nucleotides are depicted with strikethrough. FIG. 7B is a bar graph schematically depicting the concentration of [$^3$H]CH$_3$ incorporated into 1 μM of hemi-methylated DNA substrate in 15 minutes in the presence of 5.28 μM of the indicated RNA. DNMT1 was used at 10 nM. FIG. 7C is a graphical depiction of an initial velocity curve of DNMT1 activity in the presence of 0, 0.025, 0.05 and 0.1 μM of 5p-5 RNA oligo. The $K_i$ was determined to be 124.5 nM based on the velocity curve. FIG. 7D is a graphical depiction of an initial velocity curve of DNMT1 activity in the presence of 0, 0.5, 2 and 4 μM of 3p-5 RNA oligo. DNMT1 was not inhibited by 3p-5 even at the highest concentration tested.

FIG. 10A-10B shows inhibition of DNMT1 by G-quadruplex-formed telomere and superG sequence. FIG. 10A is an image following polyacrylamide gel electrophoresis of annealed telomere sequences (UUAGGGUUAGGG; SEQ ID NO:19) showing the formation of G-quadruplex structures in annealing buffer containing KCl. The G-quadruplex bands are marked by asterisks. FIG. 10B is a graphical depiction showing the inhibition of DNMT1 on hemimethylated DNA by telomere or "SuperG" (AUGGGGUGGGGU; SEQ ID NO:20) RNA molecules annealed in the presence of potassium chloride (KCl) but not when instead annealed in the presence of sodium chloride (NaCl).

FIG. 11 shows inhibition of DNMT1 by miR-155-5p with HeLAa genomic DNA as substrate. A bar graph is shown that depicts the concentration of [$^3$H]CH$_3$ incorporated by DNMT1 using human genomic DNA from the "HeLa" cell line as a substrate, in the presence or absence of 5.28 µM miR-155-5p.

FIG. 17 shows a transcriptome profile and comparison of miR-155 treated cells in a graphical depiction of a transcriptome analysis by paired-end RNA sequencing reads, as measured by fragments per kilobase per million sequenced reads, in cells transfected with miR-155-5p or a random 23-mer oligo (R23).

FIG. 18 shows a transcriptome profile and comparison of 5-azacytidine treated cells in a graphical depiction of a transcriptome analysis by paired-end RNA sequencing reads, as measured by fragments per kilobase per million sequenced reads, in cells treated with 5-azacytidine (AZA) or untreated cells (ND).

FIG. 19 shows a transcriptome profile and comparison of miR-155 and 5-azacytidine treated cells in a graphical depiction of the RNAs upregulated in cells transfected with miR-155-5p, or in cells treated with 5-azacytidine, and the degree of overlap between those two sets of RNAs.

FIG. 20 shows a transcriptome profile and comparison of miR-155 and 5-azacytidine treated cells in a graphical depiction of the RNAs downregulated in cells transfected with miR-155-5p, or in cells treated with 5-azacytidine, and the degree of overlap between those two sets of RNAs.

DETAILED DESCRIPTION

Figure 2A:
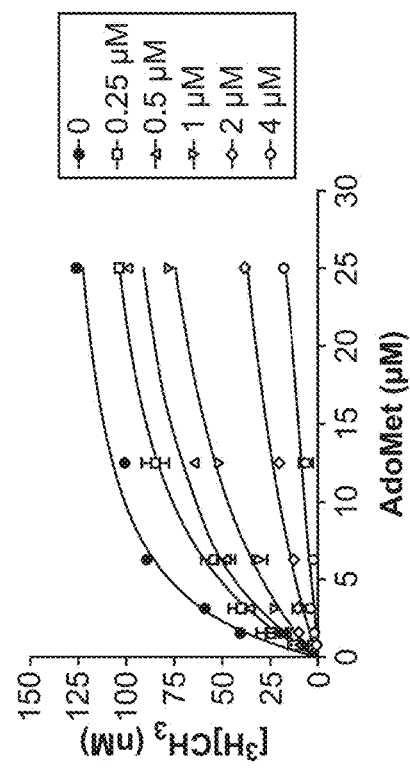

RNA molecules described herein are useful as inhibitors of DNMTs and can be incorporated into compositions and methods of inhibiting DNMTs, altering methylation patterns, increasing or restoring expression of genes downregulated by DNMT activity, and treating or preventing diseases associated with epigenetic dysregulation.

An amino acid sequence of DNMT1 corresponds to SEQ ID NO:21. A variety of other DNMT sequences are also well known, including the sequence of DNMT3A and 3B, for example, and the sequences of each of these proteins in a variety of other mammalian species. RNA molecules described herein, or an RNA molecule at least 80%, 81%, 82%, 83%, 84%, 85%, 86%, 87%, 88%, 89%, 90%, 91%, 92%, 93%, 94%, 95%, 96%, 97%, 98%, or 99% identical to an RNA molecule described herein, can be used to inhibit one or more of these DNMTs, or other proteins at least 80%, at least 85%, at least 90%, at least 95%, or at least 99% identical to one or more of them.

For example, the structure of DNMT1 and its interaction with DNA are well understood. For example, as described in Song, et al., Science, 331(6020):1036-1040 (2011), the catalytic domain of DNMT1 binds to substrate DNA, making multiple contacts along a stretch of eight consecutive nucleotides (in Song, "T1"-"A8" and their complement), with most of those contacts concentrated along a stretch of four consecutive nucleotides on a single strand (in Song, "G5"-"A8"). A separate portion of DNMT1, the CXXC domain found between the RFD and BAH domains, makes additional contacts with the DNA at a distance from the nucleotides that interact with the catalytic domain. As described in Example 1, the inhibitory RNA described herein interacts primarily with the catalytic domain. Accordingly, RNA molecules of 4-8 nucleotides in length may be sufficiently long to occupy the catalytic domain and be effective as competitive inhibitors of the protein. Longer RNA molecules can also be used, such as the RNA molecules ranging from 13-23 nucleotides in length that are described in Example 6. Although even longer RNA molecules, such as those 30 or more nucleotides in length, could also be used, it will often be more convenient to use an RNA molecule that is no more than 30 nucleotides long, having a length of, for example, 4-8 nucleotides, 4-6 nucleotides, 5-7 nucleotides, 6-8 nucleotides, 7-9 nucleotides, 8-10 nucleotides, 9-11 nucleotides, 10-12 nucleotides, 11-13 nucleotides, 12-14 nucleotides, 13-15 nucleotides, 14-16 nucleotides, 15-17 nucleotides, 16-18 nucleotides, 17-19 nucleotides, 18-20 nucleotides, 19-21 nucleotides, 20-22 nucleotides, or 21-23 nucleotides.

A wide variety of sequences of RNA molecules are capable of inhibiting a DNMT, if present at sufficient concentrations. For example, each of the RNA sequences presented in FIG. 1D inhibit DNMT1, with inhibitory constants ($K_i$) ranging from 2 µM down to about 0.1 µM. In one embodiment, the RNA molecule inhibits a DNMT such as DNMT1 with an inhibitory constant ($K_i$) in the range of between 3 µM or 2 µM down to about 0.03 µM, such as with an inhibitory constant ($K_i$) of less than 2 µM, less than 1 µM, less than 0.5 µM, less than 0.2 µM, or less than 0.1 µM.

Figure 9:
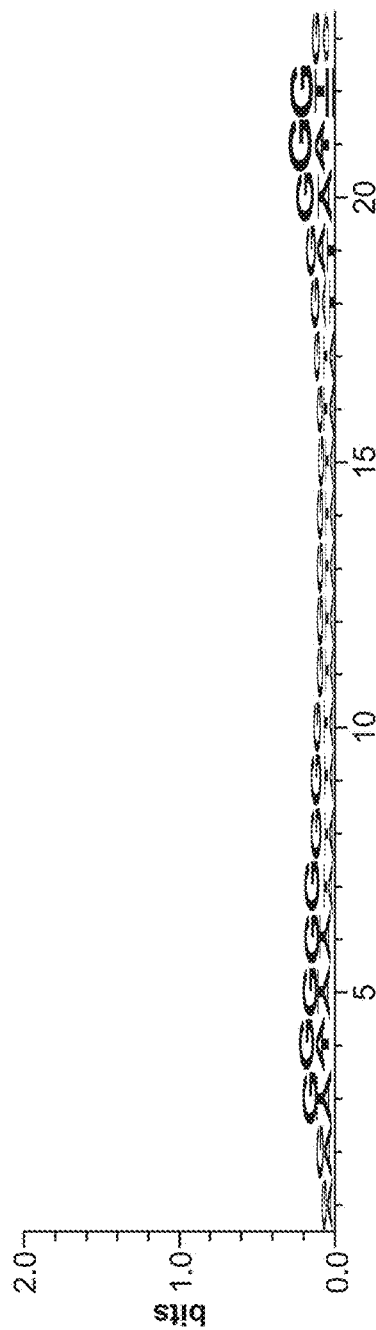
FIG. 9 shows a consensus of 7.5×10$^6$ RNAs that bind DNMT1. A graphical depiction is shown of a consensus of the nucleotide sequences of 7.5×10$^6$ RNA molecules that bind DNMT1.

RNA sequences containing guanine bases (or guanine derivatives) may have a higher affinity for DNMT and may therefore be able to inhibit its activity more efficiently, as described in Example 6 with respect to DNMT1, DNMT preferentially interacts with RNA sequences containing guanine bases near the 3' end of the molecule, as illustrated in FIGS. 9 and 10A-10B, with respect to DNMT1.

The secondary and tertiary structure of the RNA molecules described herein can also be selected to further enhance their ability to bind and inhibit DNMT1. RNA molecules having significant secondary structure (such as hairpin loops) can be used to bind and inhibit a DNMT. However, reducing or minimizing secondary structure enhances inhibition of a DNMT, as described in Example 1. In other embodiments, tertiary structure is used to enhance the ability of an RNA to inhibit a DNMT. For example, forming a G-quadruplex (or "G-tetrad") can markedly improve the ability of RNA to inhibit DNMT, as described in Example 7 with respect to DNMT1.

Compositions including an in vitro preparation of a DNMT and an RNA inhibitor of the DNMT are also described. The RNA inhibitor inhibits the activity of the DNMT on DNA, such as human DNA. The DNMT may be DNMT1. These compositions can be prepared by, for example, introducing an exogenous RNA inhibitor into a cell containing the DNMT, and isolating a preparation (e.g. a lysate) containing the DNMT and the RNA inhibitor, which may be bound together; introducing an exogenous DNMT into a cell containing the RNA inhibitor, and isolating a preparation containing the DNMT and the RNA inhibitor; or admixing a DNMT and an RNA inhibitor in vitro.

The RNA molecules described herein may be modified, for example, to enhance their stability. For example, one or more internucleotide linkages may be a phosphorothioate linkage. Alternatively, or in addition, the RNA molecule may incorporate a terminal phosphate group, such as a 5'-phosphate group, a stabilizing group such as a dTdT dimer at the 3' end, an inverted deoxy abasic moiety as a terminal cap at the 5' and/or 3' end, and/or other modifications such as a fluoro-, amino- or O-methyl-2'-ribose-modified nucleotide.

The RNA molecules described herein may be provided in an in vitro preparation in combination with a DNMT. The DNMT may be DNMT1. The in vitro preparation may result from, for example, admixing the DNMT with the RNA molecule in vitro. Alternatively, the in vitro preparation may result from isolating from a cell or cell lysate a composition containing the DNMT and the RNA molecule. For example, the cell or cell lysate may result from the exogenous expression of the DNMT in a cell containing the RNA inhibitor; the exogenous expression of the RNA inhibitor in a cell containing the DNMT; or the exogenous expression of both the RNA inhibitor and the DNMT in a cell. The RNA inhibitor may be synthetic, or produced by the transcriptional apparatus in the cell or cell lysate.

The RNA molecules may be sterile, lyophilized and packaged, or may be present in a pharmaceutically acceptable carrier. The RNA can be synthesized using standard solid phase synthesis methods, such as those using 5'-O-DMT-2'-O-t-butyldimethylsilyl(TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—$Si(iPr)_3$ (TOM), or the 5'-O-silylether-2'-ACE (5'-O-bis(trimethylsiloxy)cyclododecyloxysilylether (DOD)-2'-O-bis(2-acetoxyethoxy)methyl (ACE). Alternatively, the RNA can be synthesized in a cell following introduction of an expression vector encoding the RNA, which may be delivered by a plasmid, a virus, or by other mechanisms known in the art.

DNA viruses, such as adenoviruses or poxviruses, can be used to deliver DNA encoding the RNA molecules. DNA virus envelope proteins can also be used to package the RNA molecules themselves. RNA viruses, such as single-stranded or double-stranded RNA viruses, also can be used to deliver the RNA. Generally, the virus should be capable of delivering the RNA (or the DNA encoding it) and to infect cells (such as human cells) without replicating or integrating its DNA. In some embodiments, the RNA is packaged in a viral envelope in the partial or total absence of viral DNA or RNA.

One useful RNA virus is the hemagglutinating virus of Japan (HVJ), also called the Sendai virus, which has been developed as a safe and efficient vector. Because β-propiolactone treatment or UV-irradiation inactivates replication and transcription of genomic RNA, the HVJ envelope is extremely safe. This viral envelope or a similar biological delivery vehicle can be used for carrying inhibitory RNA to target host cells. Cell-specific targeting can be achieved by engineering the viral surface to interact with specific cell surface receptor of interest.

The RNA or expression vector may also be admixed, encapsulated, conjugated or otherwise associated with other molecules, molecule structures or mixtures of compounds, as for example, liposomes, receptor-targeted molecules, oral, nasal, rectal, topical or other formulations, for assisting in uptake, distribution and/or absorption. The RNA molecules encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compositions of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention could be prepared as SATE [(S-acetyl-2-thioethyl)phosphate] derivatives.

The RNA or expression vector may also be associated with a compound that inhibits ribonuclease ("RNase") activity. The presence of an RNase inhibitor can protect the RNA from degradation by RNase enzymes within a target cell or elsewhere. As many commercially-available RNase inhibitors are produced recombinantly (e.g. "RNase Inhibitor, Human Placenta" from New England Biolabs and "RNase Inhibitor, Murine" from New England Biolabs), the RNA or expression vector could be associated with an RNase inhibitor or with a nucleic acid encoding an RNAse inhibitor, preferably operatively associated with a promoter effective to promote the expression of the RNase inhibitor in a target cell.

Embodiments also include pharmaceutical compositions and formulations where for example, the pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Embodiments of the pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

Embodiments of the compositions may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Embodiments of pharmaceutical compositions include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention.

Formulations may include liposomal formulations. The term "liposome" as used herein refers to a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term that, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety.

Embodiments of the pharmaceutical formulations and compositions may also include surfactants.

In one embodiment, the pharmaceutical formulation may employ one or more penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants.

For topical or other administration, oligonucleotides of the invention may be encapsulated within liposomes or may form complexes thereto, in particular to cationic liposomes. Alternatively, oligonucleotides may be complexed to lipids, in particular to cationic lipids.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The compositions and formulations may be administered to a patient (e.g. a human patient) in need thereof, such as a patient having or at risk of developing a disease or condition associated with dysregulated DNA methylation. In one embodiment, therefore, the composition or formulation comprising an RNA inhibitor of DNMT as described herein is for use in treating a disease or condition associated with dysregulated DNMT activity, such as a disease or condition associated with dysregulated DNA methylation. The disease may be, for example, leukemia, a lymphoma, or a solid tumor. Specific examples of diseases that may be particularly amenable to treatment with a DNMT1 inhibitor include RCC, colorectal cancer, acute myeloid leukemia, chronic myelogenous leukemia, mixed-lineage leukemia, and glioma.

Additional diseases that may include an epigenetic component and benefit from administration of a DNMT inhibitor include, for example, Alzheimer's disease, autism, bipolar disorder, schizophrenia, asthma, kidney disease, glaucoma, or muscular dystrophy. For example, the oxytocin receptor gene was methylated in about 70% of a cohort of autism patients, compared to 40% of a control, non-autistic cohort. As oxytocin affects social interactions, restoring normal oxytocin expression may treat, relieve or prevent one or more symptoms of autism (Tsankova, et al., *Nat. Rev. Neurosci.* 8:355-67 (2007)). In other contexts, epigenetic changes have already been linked to behavioral changes. For example, rats that receive a less nurturing upbringing are more sensitive to stress throughout their lives. The sensitivity to stress is linked to a down-regulation of expression of the glucocorticoid receptor in the brain, a result of high levels of methylation in the promoter region of the glucocorticoid receptor gene (Weaver, et al., *Nat. Neurosci.* 7:847-54 (2004)). Similarly, humans who commit suicide have been observed to have lower expression of glucocorticoid receptor and increased methylation in the promoter region of the gene. Thus, administration of a DNMT inhibitor may be useful in the treatment of psychological conditions associated with stress, trauma, and/or depression.

All references cited herein, including U.S. Provisional Application No. 61/903,004 filed Nov. 12, 2013, are incorporated by reference.

EXAMPLES

Example 1: Determination of RNA Binding to Part or all of DNMT

The DNMT1 protein contains multiple domains conferring various functions on the protein. Certain of these domains are depicted in FIG. 1A, including the, RFD, BAH and catalytic domains. A series of fragments of DNMT1 were synthesized to test their ability to bind RNA. The fragments, also depicted in FIG. 1A, were synthesized as fusion proteins with glutathione S-transferase "GST".

The coding sequence of the human DNMT1 fragments were cloned into pGEX-5x-1 (GE Healthcare Life Sciences, Piscataway, N.J.) at the BamHI/EcoRI loci, and after verification by DNA sequencing, N-terminal GST fusion protein expression constructs were obtained. *Escherichia coli* strain T7 express (New England Biolabs, Ipswich, Mass.) was used to express GST-fragment 1 and 2 fusion protein and strain 10-beta (New England Biolabs, Ipswich, Mass.) was used to express GST-fragment 3, 4 and 5 fusion proteins. The protein was purified as described in Pradhan, et al., *EMBO J.* 21(4): 779-88 (2002).

The resulting protein bands are shown in FIG. 1B; asterisks mark the positions of the GST-DNMT1 fusion proteins. GST-DNMT1 fragments were adjusted to the same protein concentration with 50% slurry sepharose beads. RNase inhibitor (New England Biolabs, Ipswich, Mass.) was applied to beads slurry at 40 U/mL immediate before use.

The results of the binding assay are depicted in FIG. 1C. As shown in the figure, all 4 RNA molecules tested showed substantially greater binding to GST-DNMT1 fragment 4, containing a small portion of the second BAH domain, the GK linker and a substantial portion of the catalytic domain, than to any of the other DNMT1 fragments.

FIG. 1C shows that CEBPα-1HPE has a greater affinity for DNMT1 Fragment 4 than asCEBPα-1 does, and asCEBPα-2HPE has a greater affinity for DNMT1 Fragment 4 than asCEBPα-2. This demonstrates that nucleotide changes that disfavor the formation of RNA stem-loop structures enhance the affinity for DNMT1. Of the 4 RNA molecules tested in this experiment, the one that bound to DNMT1 most efficiently, asCEBPα-2HPE, was the one predicted to lack any stem-loop structures.

The GST-DNMT1 fragments exposed to a series of small RNA molecules are depicted in FIG. 1D. The RNA oligos were labelled at the 5' end with [γ-33P]ATP (PerkinElmer, Waltham, Mass.) using T4 polynucleotide kinase (New England Biolabs, Ipswich, Mass.), and purified with Illustra® ProbeQuant® G-50 Micro Columns (GE Healthcare Life Sciences, Piscataway, N.J.) per the manufacturer's instructions. The binding assay was performed in 50 µL reaction volume containing 20 µL of GST-DNMT1 fragment beads, 5 µL of 5 µM labelled RNA oligo, 5 µL of 10×DNMT1 reaction buffer (New England Biolabs, Ipswich, Mass.) and 20 µL of RNase-free water. After incubation at 37° C. for 10 minutes, beads were washed twice and suspended in 200 µL of PBS. The radioactivity associated with the beads was analyzed by liquid scintillation counting using a Tri-Carb® 2900TR (PerkinElmer, Waltham, Mass.). The amount of RNA oligo bound to beads were calculated by normalizing the scintillation counts of beads to that of 1 pmol labelled RNA oligo.

In FIG. 1D, the tested RNA molecules (asCEBPα-1, asCEBPα-2 and asCEBPα-1HPE) are depicted showing their optimal secondary structure calculated using the RNAfold program (Mathews, et al., *Proc Natl Acad Sci USA*, 101(19):7287-7292 (2004)). Their positional entropy when optimally folded, as calculated by the program, are written below their structures. Although these small RNAs have different structures, they have similar but not identical nucleotide sequences.

Example 2: Competitive Inhibition of DNMT on Hemimehtylated DNA by asCEBPα-2

Human full-length DNMT1 recombinant protein was expressed in a pupal ovarian cell line (Sf9) from the worm *Spodoptera frugiperda*. Sf9 cells (BD Biosciences, San Jose, Calif.) were grown in TNM-FH media (JRH Bioscience) at 27° C., 70 rpm on a Bellco steering platform to $1.0 \times 10^6$ cells/mL. Recombinant baculovirus harboring pVICHMT (Pradhan, et al., *J. Biol. Chem.* 274(46):33002-33010 (1999)) which contains DNMT1 coding sequence was used to infect the SF9 cells. The cells were cultured for 48 hour post-infection and washed once with PBS buffer after harvest.

The proteins were purified as described in Pradhan, et al. (2002). The methyltransferase reaction was also performed as described in Pradhan, et al. (2002). An assay to determine inhibition of DNMT by RNA was then performed as described below.

RNA oligo nucleotides were incubated at 20 µM in 50 µL volume containing 10 mM Tris-HCl (pH 8.0) and 100 mM NaCl by incubating at 95° C. for 2 minutes, 65° C. for 5 minutes, 45° C. for 10 minutes, 37° C. for 10 minutes and 25° C. for 10 minutes.

For determination of the inhibition pattern and $K_i$ of asCEBPα-2 versus hemimethylated DNA substrate, 20 nM of the DNMT1 enzyme was incubated with 1.328, 0.884, 0.59, 0.394, 0.262, 0.1748 and 0.1168 µM (concentration calculated in terms of hemimethylated CpG) of the 36-bp length hemimethylated DNA substrate with the sequence of $(C_{Me}GG \cdot CCG)_{12}$ and 5.328 µM of [$^3$H]AdoMet (PerkinElmer, Waltham, Mass.) in the presence of 0, 0.25, 0.5, 1, 2 and 4 µM folded asCEBPα-2 inhibitor RNA in 1×DNMT1 reaction buffer (New England Biolabs, Ipswich, Mass.). The reaction was performed at 37° C. for 30 minutes and DNMT1 enzyme was quenched by flash freezing the reaction mix in a dry ice-methanol bath. The reaction was split into two halves and spotted onto DE81 Whatman® 3658-325 ion exchange filter papers (GE Healthcare Life Sciences, Piscataway, N.J.). The Ki and velocity plots were calculated according to Bacolla, et al., *J. Biol. Chem.*, 274:33011-33019 (1999).

As shown in FIG. 2A, asCEBPα-2 effectively inhibited DNMT1 activity on the hemimethylated DNA substrate in a dose-dependent manner, with noticeable activity at a concentration of 0.25 µM and increasing activity at each of the higher concentrations through 4 µM. As shown in the double reciprocal plot shown in FIG. 2C, asCEBPα-2 was determined to competitively inhibit DNMT1 activity, as each of the lines in the plot converge at zero on the X-axis. As shown in FIG. 2E, $K_m^{app}$ versus RNA concentration was fitted to a linear regression, permitting a determination of $K_i$ as the absolute value of x where y=0 in the linear regression function.

Figure 2B:
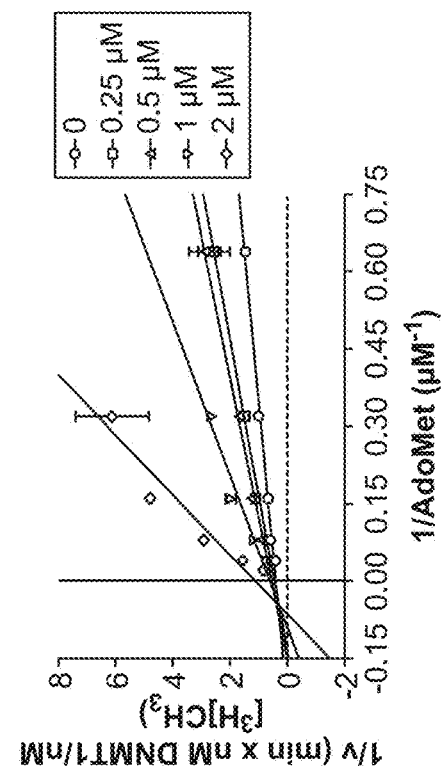
Figure 2C:
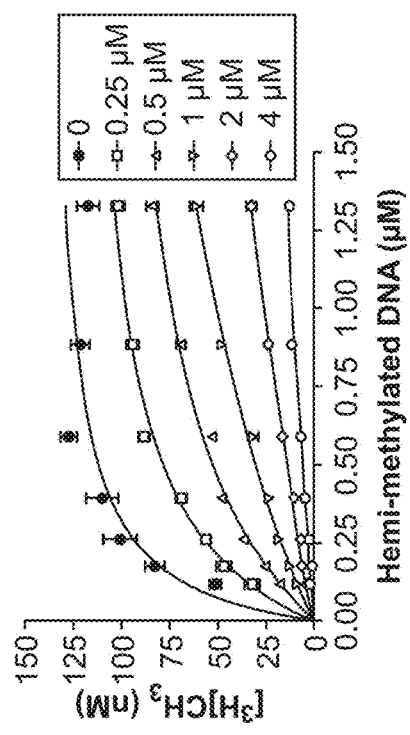
Figure 2D:
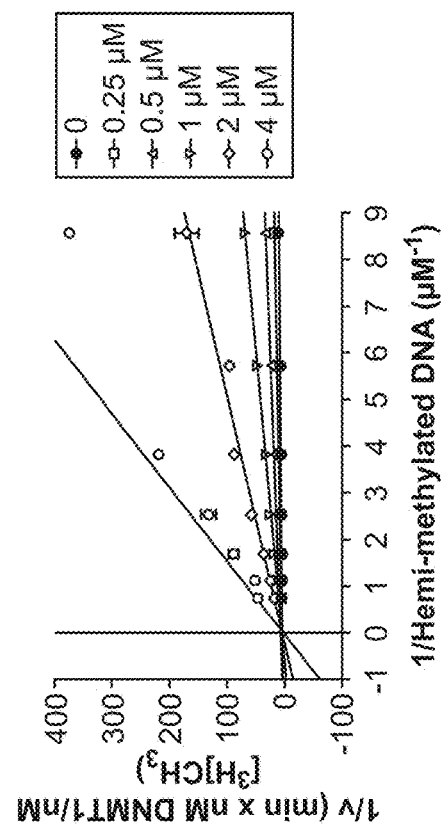

For determination of the inhibition patterns of various test RNAs and $K_i$ for asCEBPα-2 versus AdoMet, reactions were carried out at similar conditions as those described above. 20 nM of enzyme was incubated with 2 µM of hemimethylated DNA substrate and 0.78125, 1.5625, 3.125, 6.25, 12.5 and 25 µM of mixed cold and hot AdoMet (18.5:1 in terms of molar ratio) in the presence of 0, 0.25, 0.5, 1, 2 and 4 µM folded asCEBPα-2 inhibitor RNA in 1×DNMT1 reaction buffer. Reaction and sample processing were performed the same as that of hemimethylated DNA competitive assays. The nanomolar [³H]CH₃ transferred to hemimethylated DNA substrate was calculated in the same way as in the competitive experiment versus hemimethylated DNA substrate, except that the nanomolar concentration obtained was multiplied by an coefficient of 19.5. The results are depicted in FIG. 2B. The inhibition pattern of asCEBPα-2 versus AdoMet was mixed inhibition as indicated by the double reciprocal curve shown in FIG. 2D, as the lines converged at a point less than zero on the X-axis. As shown in FIG. 2F, the slope of the double reciprocal curve versus RNA concentration was fitted to a linear regression, permitting a determination of $K_i$ as the absolute value of x where y=0 in the linear regression function.

Similar experiments revealed that asCEBPα-1 asCEBPα-1HPE, and asCEBPα-2HPE also competitively inhibit DNMT1 activity on a hemimethylated DNA substrate. For each of these RNA molecules, including asCEBPα-2, the $K_i$ calculated for inhibition on the hemimethylated DNA substrate is shown in Table 1. The Ki is also provided for micro RNAs which differ from asCEBPα-1 and its variants by structure, size and sequence. Inhibition of DNMTs is observed in all cases.

The $K_i$ calculated for inhibition on the hemimethylated DNA substrate for each of the 14 miRNAs is also shown in Table 1.

TABLE 1

Inhibition pattern of DNMT1 by miRNAs

| Variable substrate | Fixed substrate | Inhibitor | Type of inhibition | $K_i$ (µM) |
|---|---|---|---|---|
| $(C_{Me}GG \cdot CCG)_{12}$ | AdoMet | asCEBPα-1 | competitive | 2.003 |
| $(C_{Me}GG \cdot CCG)_{12}$ | AdoMet | asCEBPα-1HPE | competitive | 0.9175 |
| $(C_{Me}GG \cdot CCG)_{12}$ | AdoMet | asCEBPα-2 | competitive | 0.4341 |
| $(C_{Me}GG \cdot CCG)_{12}$ | AdoMet | asCEBPα-2HPE | competitive | 0.1352 |
| $(C_{Me}GG \cdot CCG)_{12}$ | AdoMet | miR-9-5p | competitive | 0.4926 |
| $(C_{Me}GG \cdot CCG)_{12}$ | AdoMet | miR-17-5p | competitive | 0.3172 |
| $(C_{Me}GG \cdot CCG)_{12}$ | AdoMet | miR-21-5p | competitive | 1.291 |
| $(C_{Me}GG \cdot CCG)_{12}$ | AdoMet | miR-92a-1-5p | competitive | 0.4756 |
| $(C_{Me}GG \cdot CCG)_{12}$ | AdoMet | miR-92a-3p | competitive | 1.65 |
| $(C_{Me}GG \cdot CCG)_{12}$ | AdoMet | miR-127-3p | competitive | 0.2694 |
| $(C_{Me}GG \cdot CCG)_{12}$ | AdoMet | miR-155-5p | competitive | 0.02788 |
| $(C_{Me}GG \cdot CCG)_{12}$ | AdoMet | miR-9-3p | competitive | 1.602 |
| $(C_{Me}GG \cdot CCG)_{12}$ | AdoMet | miR-16-5p | competitive | 0.4633 |
| $(C_{Me}GG \cdot CCG)_{12}$ | AdoMet | miR-19b-3p | competitive | 3.323 |
| $(C_{Me}GG \cdot CCG)_{12}$ | AdoMet | miR-20a-5p | competitive | 0.5605 |
| $(C_{Me}GG \cdot CCG)_{12}$ | AdoMet | miR-145-5p | competitive | 2.458 |
| $(C_{Me}GG \cdot CCG)_{12}$ | AdoMet | miR-146a-5p | competitive | 1.031 |
| $(C_{Me}GG \cdot CCG)_{12}$ | AdoMet | miR-373-5p | competitive | 0.2977 |
| AdoMet | $(C_{Me}GG \cdot CCG)_{12}$ | asCEBPα-2 | mixed | 0.09166 |
| AdoMet | $(C_{Me}GG \cdot CCG)_{12}$ | miR-17-5p | mixed | 0.3846 |

Paralleling the results observed in the GST-DNMT1 protein binding assays, asCEBPα-1HPE proved a more effective inhibitor than asCEBPα-1, and asCEBPα-2HPE more effective than asCEBPα-2 or either of the other two RNA molecules, with a $K_i$ as low as about 0.14 µM. Overall the $K_i$ values in Table 1 ranged from about 3.3 µM for miR-19b-3p to about 0.03 µM for miR-155-5p.

Example 3: Inhibition of DNMT by microRNAs

MicroRNAs were tested for their ability to inhibit human DNMT1; asCEBPα-1, asCEBPα-1HPE, asCEBPα-2, and asCEBPα-2HPE were also included for comparison.

TABLE 2

Sequences of miRNAs

| Inhibitor | Sequence | SEQ ID NO: |
|---|---|---|
| asCEBPα-1 | CCGGGACGCAGGCGGCGUCAGGC | 1 |
| asCEBPα-1HPE | CCGGGAAGCAGGCGGCGUCAGGC | 2 |
| asCEBPα-2 | GCCAGUGGCGAGGGGCGGCGCGG | 3 |
| asCEBPα-2HPE | GACAGUGGAGAGGGGCGGAGCGG | 4 |
| miR-9-5p | UCUUUGGUUAUCUAGCUGUAUGA | 22 |
| miR-17-5p | CAAAGUGCUUACAGUGCAGGUAG | 23 |
| miR-21-5p | UAGCUUAUCAGACUGAUGUUGA | 24 |
| miR-92a-1-5p | AGGUUGGGAUCGGUUGCAAUGCU | 25 |
| miR-92a-3p | UAUUGCACUUGUCCCGGCCUGU | 26 |

TABLE 2-continued

Sequences of miRNAs

| Inhibitor | Sequence | SEQ ID NO: |
|---|---|---|
| miR-127-3p | UCGGAUCCGUCUGAGCUUGGCU | 27 |
| miR-155-5p | UUAAUGCUAAUCGUGAUAGGGGU | 5 |
| miR-9-3p | AUAAAGCUAGAUAACCGAAAGU | 28 |
| miR-16-5p | UAGCAGCACGUAAAUAUUGGCG | 29 |
| miR-19b-3p | UGUGCAAAUCCAUGCAAAACUGA | 30 |
| miR-20a-5p | UAAAGUGCUUAUAGUGCAGGUAG | 31 |
| miR-145-5p | GUCCAGUUUUCCCAGGAAUCCCU | 32 |
| miR-146a-5p | UGAGAACUGAAUUCCAUGGGUU | 33 |
| miR-373-5p | ACUCAAAAUGGGGCGCUUUCC | 34 |

Single point biochemistry assays were performed by incubating 10 nM of the DNMT1 enzyme with 1 µM of hemi-methylated DNA and 5.328 µM of [$^3$H]AdoMet in the presence of 5.28 µM of folded synthetic miRNA oligos. The reaction was done for 15 minutes and radioactivity was counted. The [$^3$H]AdoMet incorporated was calculated as described in Example 2.

Figure 3B:
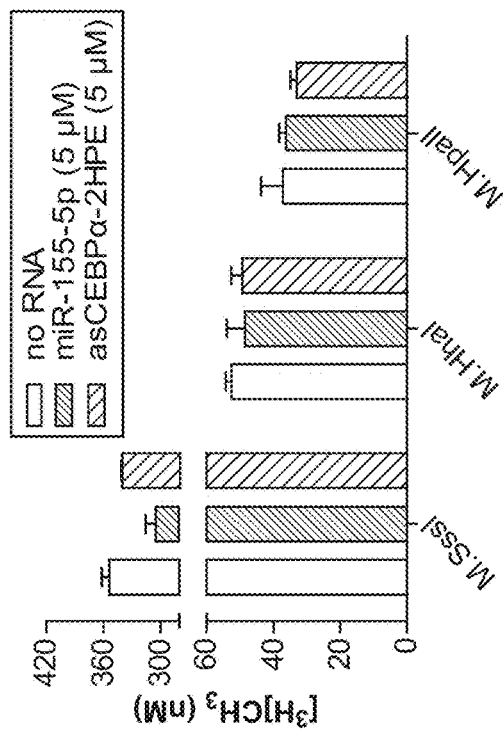
FIG. 3A-3B shows that miRNAs inhibit DNMT1 activity but not bacterial DNA methyltransferase activity.
Figure 3A:
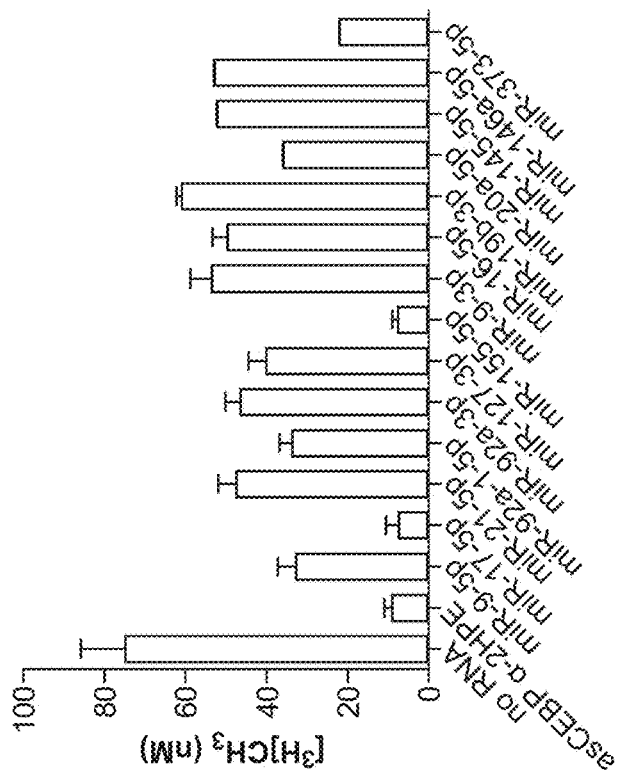
Figure 4B:
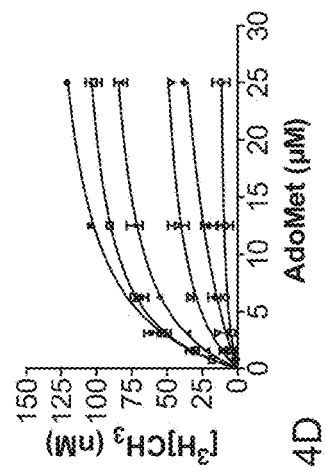
FIG. 4A-4D shows inhibition patterns of DNMT1 activity by representative microRNA, miR-17-5p, versus hemimethylated DNA and AdoMet substrates.
Figure 4A:
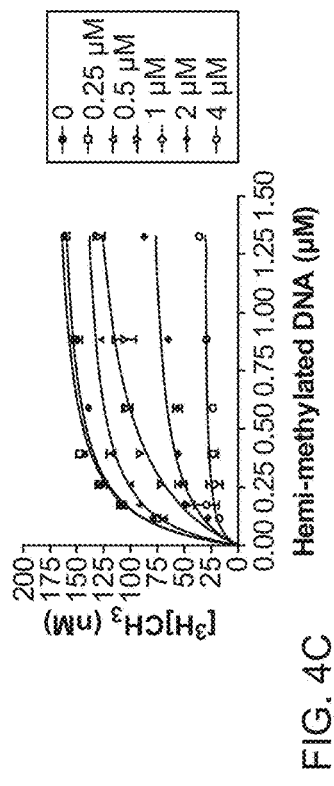
Figure 4D:
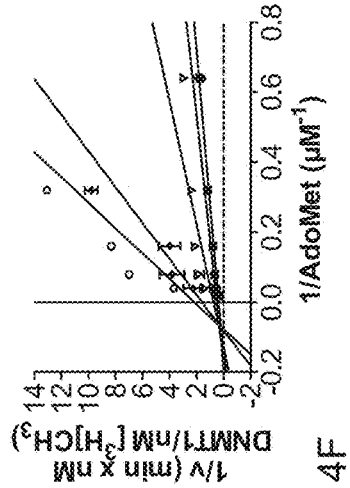
Figure 4C:
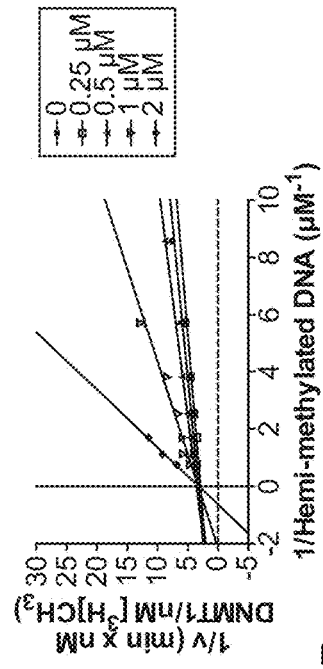
Figure 4F:
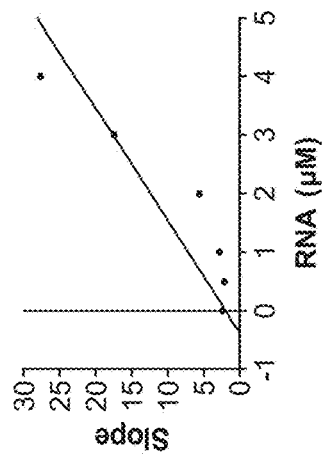
FIG. 4F is a representative figure depicting the deduction of $K_i$ in miR-17-5p versus AdoMet mixed inhibition studies. The y axis values, slopes, are the slopes of the double reciprocal plots in FIG. 4D.
Figure 4E:
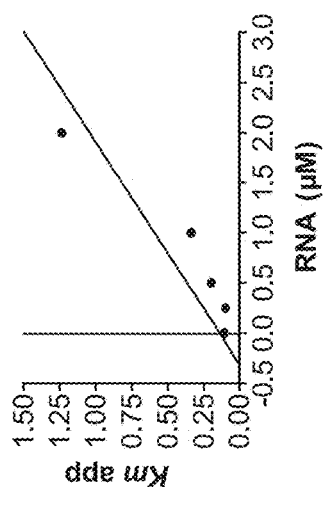
FIG. 4E is a representative figure depicting the deduction of $K_i$ in miR-17-5p versus hemimethylated DNA competitive inhibition studies. $K_m^{app}$ is obtained from the nonlinear regression of curves in FIG. 4A.
Figure 5A:
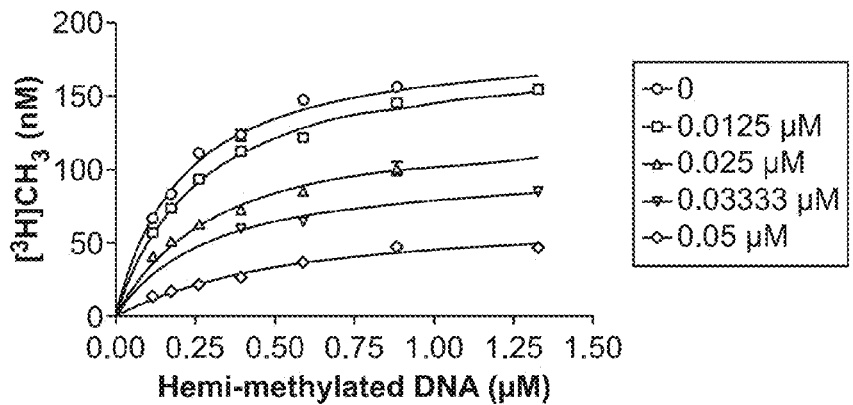
FIG. 5A-5C shows a determination of the $K_i$ of the most potent inhibitory microRNA, miR-155-5p, versus hemimethylated DNA substrate.
Figure 5B:
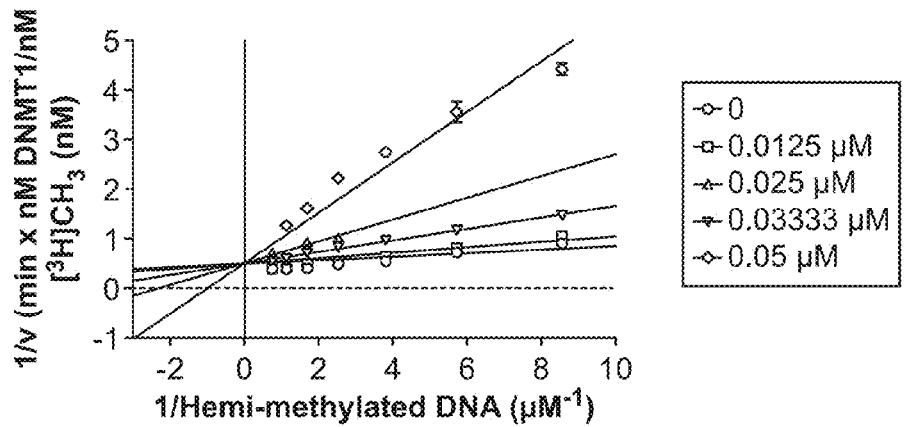
Figure 5C:
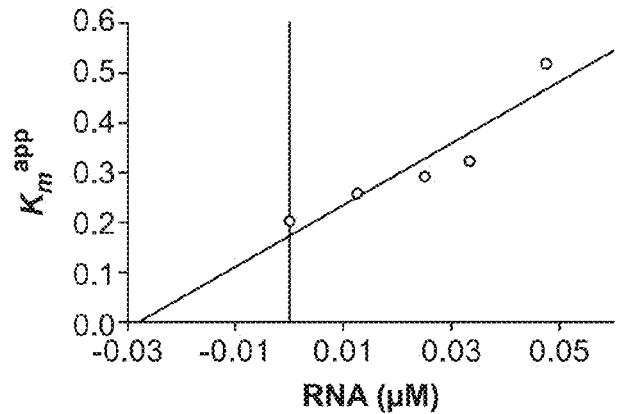

As shown in FIG. 3A, each of the tested microRNAs was able to inhibit DNMT1, although with noticeable variation in efficacy.

Two of the most efficient DNMT1 inhibitors, asCEBPα-2HPE and miR-155-5p, were tested to see if they similarly inhibit bacterial DNA methyltransferases. 0.08 U/µL M.SssI, 0.5 U/µL M.HhaI or 0.08 U/µL M.HpaII methyltransferases were incubated with 2 ng/µL of pUC19 DNA and 5.328 µM of [$^3$H]AdoMet in the presence of 5 µM of folded synthetic miRNA oligos. The reaction was done for 30 minutes and radioactivity was counted. [$^3$H]AdoMet incorporated was calculated as described in Example 2.

The inhibitory activity of each of the 14 miRNAs listed in Table 2 were also tested using single point biochemistry assays to determine their ability to inhibit DNMT as described above using hemimethylated DNA and AdoMet substrates. Representative plots for miR-17-5p and miR-155-5p are depicted in FIGS. 4A-4F and 5A-5C, respectively.

As shown in FIG. 3B, the human DNMT1 inhibitors demonstrated little to no inhibition of any of the three bacterial methyltransferases under the conditions of the experiment.

Example 4: The RNA Molecules Efficiently Inhibit DNMT Even after Addition of Extra Hemimethylated DNA Substrate 20 nM of DNMT1 enzyme was pre-incubated with 2 µM of miR-17-5p or 0.05 µM of miR-155-5p at 37° C. for 10 minute in 1×DNMT1 reaction buffer. The reaction mix was then supplemented with 5.328 µM of [$^3$H]AdoMet and increasing concentrations of hemimethylated DNA (0.25, 0.5, 1.5, 2, 3, 4 and 10 µM), and was incubated at 37° C. for 30 minutes. DNMT1 was quenched and the concentration of [$^3$H]CH$_3$ transferred to the hemimethylated DNA substrate was analyzed in the same way as in example 2. Reactions without RNA pre-incubation were used as a control.

Figure 6:
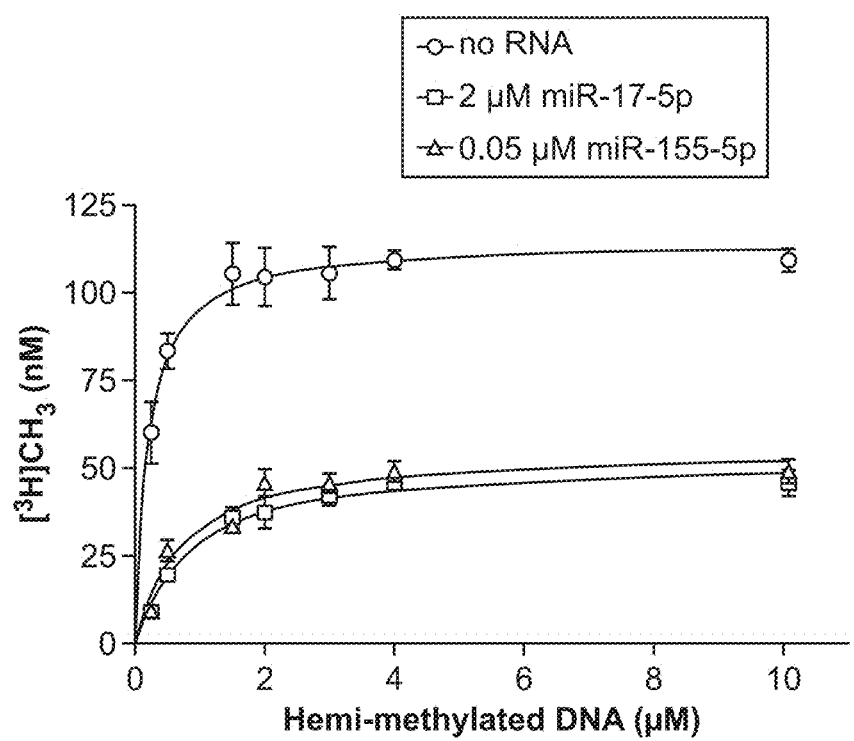
FIG. 6 shows that increasing hemi-methylated DNA cannot derepress miRNA based inhibition. A graphical depiction is shown of a velocity curve of 20 nM of DNMT1 pre-incubated with 2 μM of miR-17-5p or 0.05 μM of miR-155-5p or with no RNA (negative control). Only about 50% of DNMT1 catalytic activity was retained even when the concentration of hemimethylated DNA substrate was as high as 10 μM.

As shown in FIG. 6, even the addition of 10 µM of substrate failed to restore more than half of the activity of the DNMT1 pre-incubated with 2 µM of miR-17-5p or 0.05 µM of miR-155-5p.

Example 5: Substantially Shorter RNA Molecules Effectively Inhibit DNMT

Single point biochemistry assays were performed by incubating 10 nM of the DNMT1 enzyme with 1 µM of hemimethylated DNA and 5.328 µM of [$^3$H]AdoMet in the presence of 5.28 µM of folded synthetic RNA oligos. The reaction was done for 15 minutes and radioactivity was counted. [$^3$H]AdoMet incorporation, initial velocity curve and $K_i$ were calculated as described in Example 2.

The effect of a series of truncations or internal deletions of miR-155-5p is shown in FIG. 7A-7D. As shown in FIG. 7B, most of the deletion mutants tested retained the ability to inhibit DNMT1. All of the deletions at the 5' end retained inhibitory activity, including 5p-5 in which the first 10 nucleotides were deleted, reducing the size of the RNA from 23 nucleotides to 13 nucleotides. Indeed, in FIG. 7B, 5p-5 demonstrated an inhibitory activity similar to that of miR-155-5p. Each of the internal truncations tested were also effective inhibitors of DNMT1 on hemimethylated DNA. At the 3' end, a truncation of the last two nucleotides was tolerated, although with some loss of inhibitory efficacy; truncations of four or more nucleotides substantially prevented the resulting RNA from effectively inhibiting DNMT1 under the conditions tested.

FIGS. 7C and 7D are representative plots of the inhibitory activity of 5p-5 and 3p-5 at increasing concentrations. FIG. 7C shows an initial velocity curve of DNMT1 activity in the presence of 0, 0.025, 0.05 and 0.1 µM of 5p-5 RNA oligo. The $K_i$ was determined to be 124.5 nM. FIG. 7D shows an initial velocity curve of DNMT1 activity in the presence of 0, 0.5, 2 and 4 µM of 3p-5 RNA oligo; DNMT1 was not inhibited by 3p-5 even at the highest concentration tested.

Example 6: Binding Site Selection Assays for Identifying RNA Molecules that Bind DNMT1

Recombinant full length DNMT1 was produced from a baculovirus expression system (Sf9 cells) and protein was extracted with chitin agarose beads (New England Biolabs, Ipswich, Mass.). A synthetic RNA library was constructed that was 23 nucleotides long with a randomized RNA base at each position (Integrated DNA Technologies, Coralville, Iowa). 80 µM of this randomized RNA library was then incubated with 2.8 µM of recombinant DNMT1 still bound to the chitin beads in 1×DNMT1 enzymatic buffer (New England Biolabs, Ipswich, Mass.) for 1 hour at 37° C. with gentle agitation. DNMT1/Chitin beads were then washed 6 times with 1×DNMT1 buffer (200 µl). RNA was eluted by incubating the sample in 117 µl of 1×RIP™ wash buffer, 15 µl of 10% SDS and 18 µl of Proteinase K (All provided by Milipore, Billerica, Mass.) at 55° C. for 30 minutes with agitation. 400 µl of Phenol/Chloroform/Isoamyl alcohol (125:24:1 ratio for RNA extraction) was directly added to the sample and then vortexed for 15 seconds. Sample was centrifuged at 14,000 RPM for 10 minutes at room temperature to separate the phases. 350 µl of the aqueous phase was carefully removed and 400 µl of chloroform was added and sample was vortexed for 15 seconds. The sample was then centrifuged at 14,000 RPM for 10 minutes at room temperature. 300 μl of aqueous phase was collected and small RNAs were precipitated. 5 ng of the extracted 23 nucleotide long synthetic RNA was then used to create a small RNA library for Illumina® next-generation sequencing per manufacturers specifications (New England Biolabs, Ipswich, Mass.), except that small RNA was 5' phosphorylated with T4 PNK (New England Biolabs, Ipswich, Mass.) after ligation of the 3' sequencing adapter. T4 PNK was heat inactivated at 75° C. before proceeding to the next step in the NEB small RNA library preparation. Quality of the small RNA library was confirmed by Agilent Bioanalyzer® (Agilent, Santa Clara, Calif.) analysis and was then sequenced on an Illumina MiSeq® system (25 base single end reads) (Illumina, San Diego, Calif.). $7.45 \times 10^6$ sequencing reads were recovered from the sequencer that corresponded to randomized synthetic RNA, 23 nucleotides in length, bound to recombinant DNMT1. A small number of sequencing reads were also recovered that corresponded to endogenous Sf9 rRNAs. Subsequent data analysis, including sequence logo analysis, was done within the open source software suite Galaxy.

The five randomized RNA sequences recovered most frequently in the binding site selection assay had the following sequences:

TABLE 3

| | |
|---|---|
| AGGACGUGCGCGGCGGAGAGCGC | (SEQ ID NO: 35) |
| AGUUCGAUGUCGGGGCUCGGAAU | (SEQ ID NO: 36) |
| AACGAGUAGGACGUGCGCGGCGG | (SEQ ID NO: 37) |
| AAAAGGGAACGUGAGCUGGGUUU | (SEQ ID NO: 38) |
| AGCGAACAAGUACCGUGAGGGAA | (SEQ ID NO: 39) |

These were aligned with miR-155-5p and miR-17-5p to yield the following consensus sequence for DNMT1 inhibitors 23 nucleotides in length:

(SEQ ID NO: 40)
(A/C/U)(A/G/U)N(A/G/U)N(A/G/U)NNNNNN(G/A/C)N(G/U)

Figure 8:
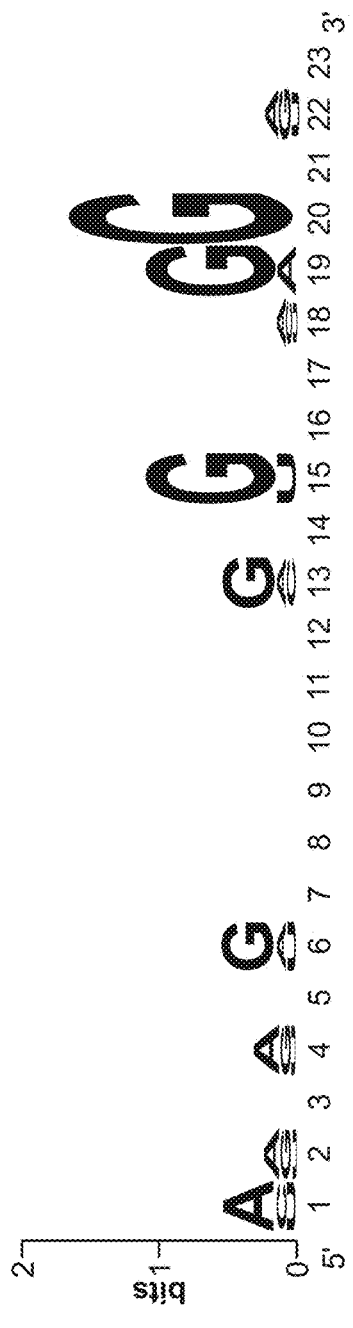
FIG. 8 shows a consensus of 7 RNAs that strongly bind DNMT1 by a graphical depiction of a consensus of the nucleotide sequences of seven highly representative RNA molecules.

NN(A/C/G)(A/G)GN(A/G/U)N where N can be any nucleotide. A graphical depiction of the consensus is represented in FIG. 8. Importantly, Example 5 demonstrated that none of the first 10 nucleotides are required for DNMT1 inhibition. In contrast, all seven of the sequences included in the consensus contained a guanine four bases from the 3' end, and most also contained a guanine five bases from the 5' end.

A graphical depiction of all of the randomized RNA sequences recovered in the binding site selection assay is shown in FIG. 9. As shown in FIG. 9, a marked preference for guanine is observed near the 3' end of the RNA, particularly at the second, third, fourth and fifth positions from the 3' end; cytosine appears to be markedly disfavored at these positions.

Example 7: G-Quadruplex Structures Inhibit DNMT-1 Activity

In view of the preference for guanine residues in RNA molecules binding to DNMT1, an experiment was performed to determine whether G-quadruplex structures contribute to DNMT1 inhibition.

In contrast to a double-helix, in which one base on one strand of a nucleic acid interacts with one base on another nucleic acid strand through the formation of hydrogen bonds, a G-quadruplex is a structure involving hydrogen bonding among four guanine bases. Thus, unlike a double-helix involving two nucleic acid strands, a G-quadruplex can involve four distinct nucleic acid strands. Alternatively, some or all of the four strands of a G-quadruplex may be linked to each other, in which case rather than being a tetramolecular structure, the structure may be intramolecular, bimolecular, or trimolecular.

Typically, a cation (a positively charged ion) is present at the center of the structure formed by the four guanine bases. Specifically, the presence of a potassium ion ($K^+$) at the center promotes G-quadruplex formation more effectively than sodium ($Na^+$) or lithium ($Li^+$) ions do.

G-quadruplex formation is more frequently observed in G-rich nucleic acid sequences. In particular, where multiple, adjacent guanines are observed, a G-quadruplex structure may form in which one group of four interacting guanines is layered atop another group of four interacting guanines. G-quadruplex formation can also promoted or stabilized using an appropriate crosslinker (see, e.g., Muller, et al., Nature Chem., 2:1095-1098 (2010)) and has been observed at telomeres (see, e.g., Paeschke, et al., Nature Structural & Mol. Biol., 12(10):847-854 (2005)).

RNA oligos containing G-quadruplexes were obtained by annealing in the presence of 10 mM Tris-HCl (pH 8.0), 100 mM KCl and 2 mM MgCl2. G-quadruplex-free oligos were folded in the presence of 10 mM Tris-HCl (pH 8.0) and 100 mM NaCl. The annealing temperature gradient used was the same as in Example 2. Immediate after annealing, oligos were resolved on a 20% polyacrylamide gel in TBE buffer. Gels were stained by SYBR® Gold (Life technologies, Grand Island, N.Y.), and bands were visualized with a Typhoon® 9400 scanner (Amersham Biosciences, Piscataway, N.J.). As shown in FIG. 10A, an RNA telomere sequence (SEQ ID NO:19) formed G-quadruplex structures when annealed in KCl (asterisks), but not when instead annealed in NaCl.

To test DNMT1 inhibition, 1 μM of hemimethylated DNA and 5.328 μM of [$^3$H]AdoMet substrate were incubated with 10 nM of DNMT1 enzyme in the presence of G-quadruplex-containing or G-quadruplex-free RNA oligos at 37° C. for 15 minutes. Incorporated [$^3$H]AdoMet was calculated as described in Example 2. As shown in FIG. 10B, both the RNA telomere sequence and an RNA "SuperG" sequence (SEQ ID NO:20) inhibited DNMT1 when annealed in KCl, but not when instead annealed in NaCl, suggesting that RNA molecules forming a G-quadruplex can inhibit DNMT1.

Example 8: Impact of RNA Length on FNMT Inhibition

The ability of miR-155-5p to inhibit DNMT1 was tested in the context of human genomic DNA. Single point biochemistry assay was carried out as described in example 3 except that 600 ng of purified HeLa genomic DNA was used as substrate.

As shown in FIG. 11, in the presence of 5.28 μM miR-155-5p, about half of the methylation activity of DNMT1 on HeLa genomic DNA was retained, indicating that miR-155-5p can also potently inhibit DNMT1 activity in the context of genomic DNA. Importantly, this establishes that the inhibition of DNMT1 by miR-155-5p globally affects genomic DNA methylation, rather than being a target-specific phenomenon dependent on the transcription of a particular target gene, or on the ability of the inhibitory RNA to form a complex with a messenger RNA from a specific target of DNMT1 activity.

Example 9: The Genome in Colorectal Cancer Cells Contained Altered DNA Methylation Determined by Use of Exogenous microRNAs Exogenous miR-155-5p causes significant DNA hypomethylation of human colorectal cancer genome. To determine the effect of microRNA on genomic methylation alteration, we transfected a random 23-mer RNA oligo and miR-155-5p separately into human colorectal cancer cell line HCT-116, and compared the DNA methylation in the genome of transfected cells using reduced representation bisulfite sequencing (RRBS) analysis. Libraries were sequenced on an Illumina GAII platform (Illumina, San Diego, Calif.). Of each biological replicate, about 30 million of 72 bp high-quality paired-end reads (Phred score≥20, adaptor trimmed) were mapped uniquely to human genome hg19. With a minimum read coverage threshold of 10, 4,896,172 CpG sites were commonly covered by the four RRBS libraries, which represent about 9% of the total CpG sites in human genome.

Figure 12:
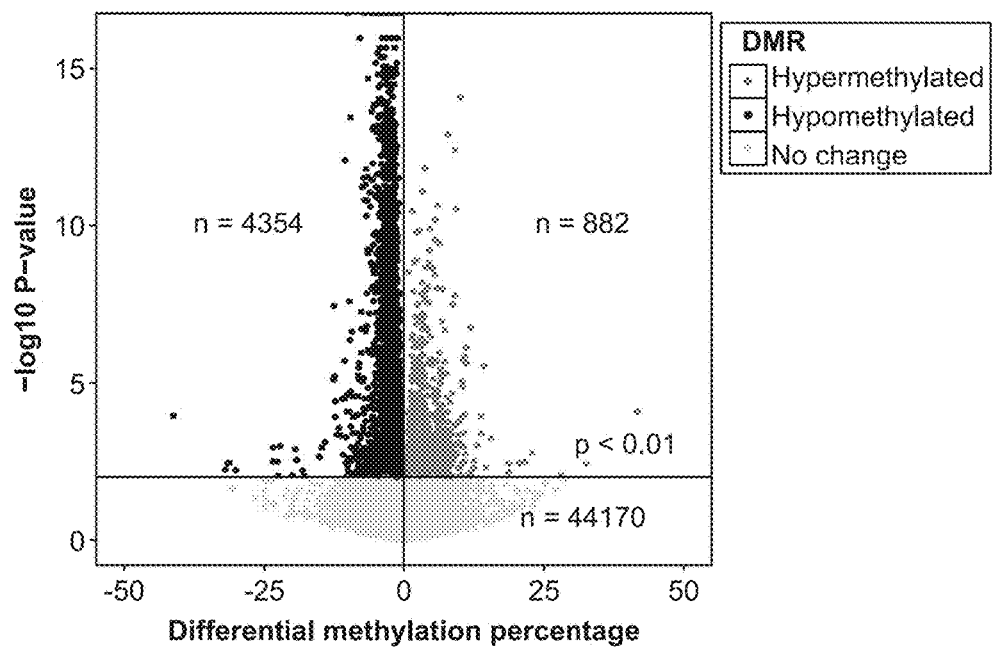
FIG. 12 shows a genome wide CpG methylation analysis using RRBS in a graphical depiction comparing CpG methylation, as assessed by reduced representation bisulfite sequencing, in cells transfected with miR-155-5p versus a random 23-mer oligo. The x-axis represents the percentage increase (or decrease) in methylation observed in cells transfected with miR-155-5p; the y-axis represents statistical significance, represented as $-\log_{10}$ (P-value).

Differential methylation analysis was performed on single CpG sites as well as 50 kb and 10 kb tiles. Of the 49406 non-overlapped 50 kb genome tiles analyzed, 4354 tiles (8.8% of total tiles) showed hypomethylation in the cells transfected by miR-155-5p with a mean demethylation rate of 2.4%, while 882 tiles (1.8% of total tiles) showed hypermethylation with a mean methylation change rate of 4.0% (logistic regression test, p<0.01). We demonstrate that miR-155-5p cause genome wide demethylation since the number of hypomethylated tiles is higher than that of hypermethylated tiles (FIG. 12).

Figure 13:
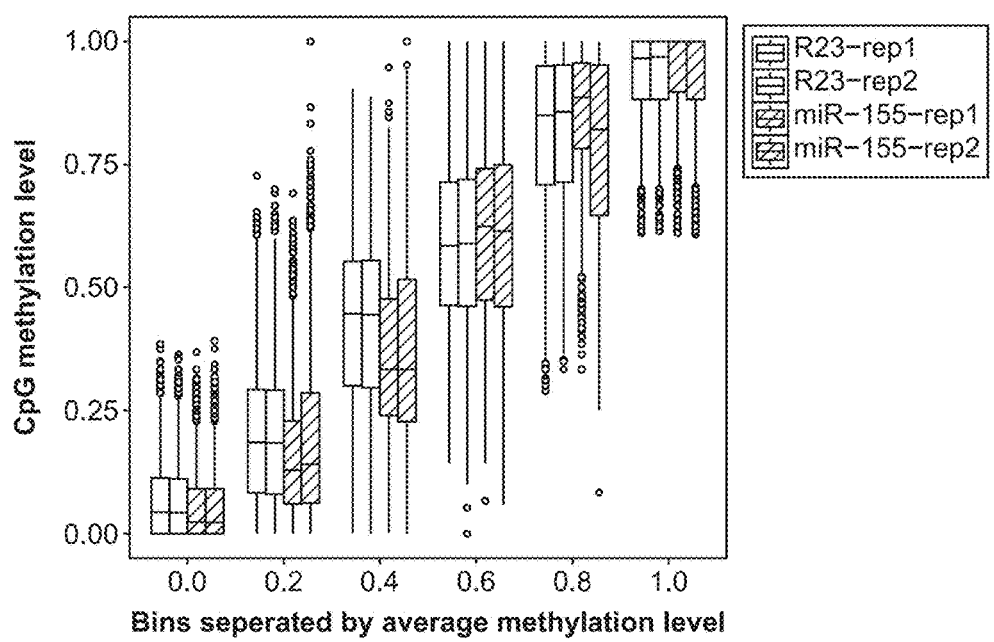
FIG. 13 shows a genome wide CpG methylation analysis using RRBS in a graphical depiction of miR-155-5p-induced differences in CpG methylation for each of six categories of CpG sites, ranging from those with the lowest average methylation (bin "0") to highest average methylation (bin "1").

At single base resolution level, 55,225 differentially methylated CpG sites were separated into six bins based on their average methylation level in the four libraries (FIG. 13). Mean methylation level were significantly lower in the medium-to-low range (bin 0, average demethylation 1.24%, p=0.005, t-test; bin 0.4, average demethylation 6.36%, p=0.007, t-test; other bins are not significantly different) with the most robust demethylation (6.36%) occurring at bin 0.4 (FIG. 13), and bin 0.4 represents 10.2% of the total differentially methylated sites. Based on these data, we conclude that miR-155-5p mediated genome-wide demethylation occurs at the medium-to-low methylated CpG sites.

Figure 14:
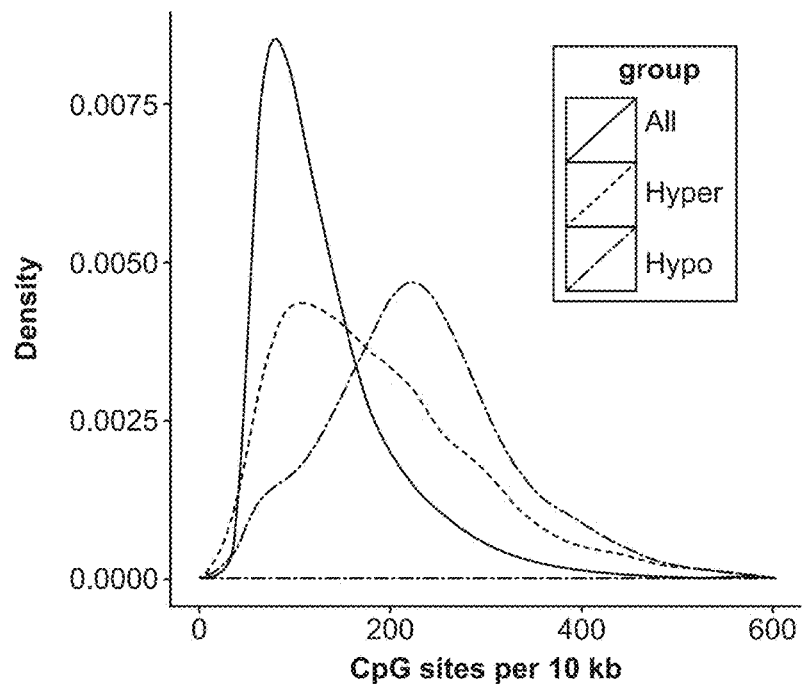
FIG. 14 shows genome wide CpG methylation analysis using RRBS is a graphical depiction of the density, measured in CpG sites per 10 kb of differentially methylated sites in cells transfected with miR-155-5p versus a random 23-mer oligo.
Figure 16:
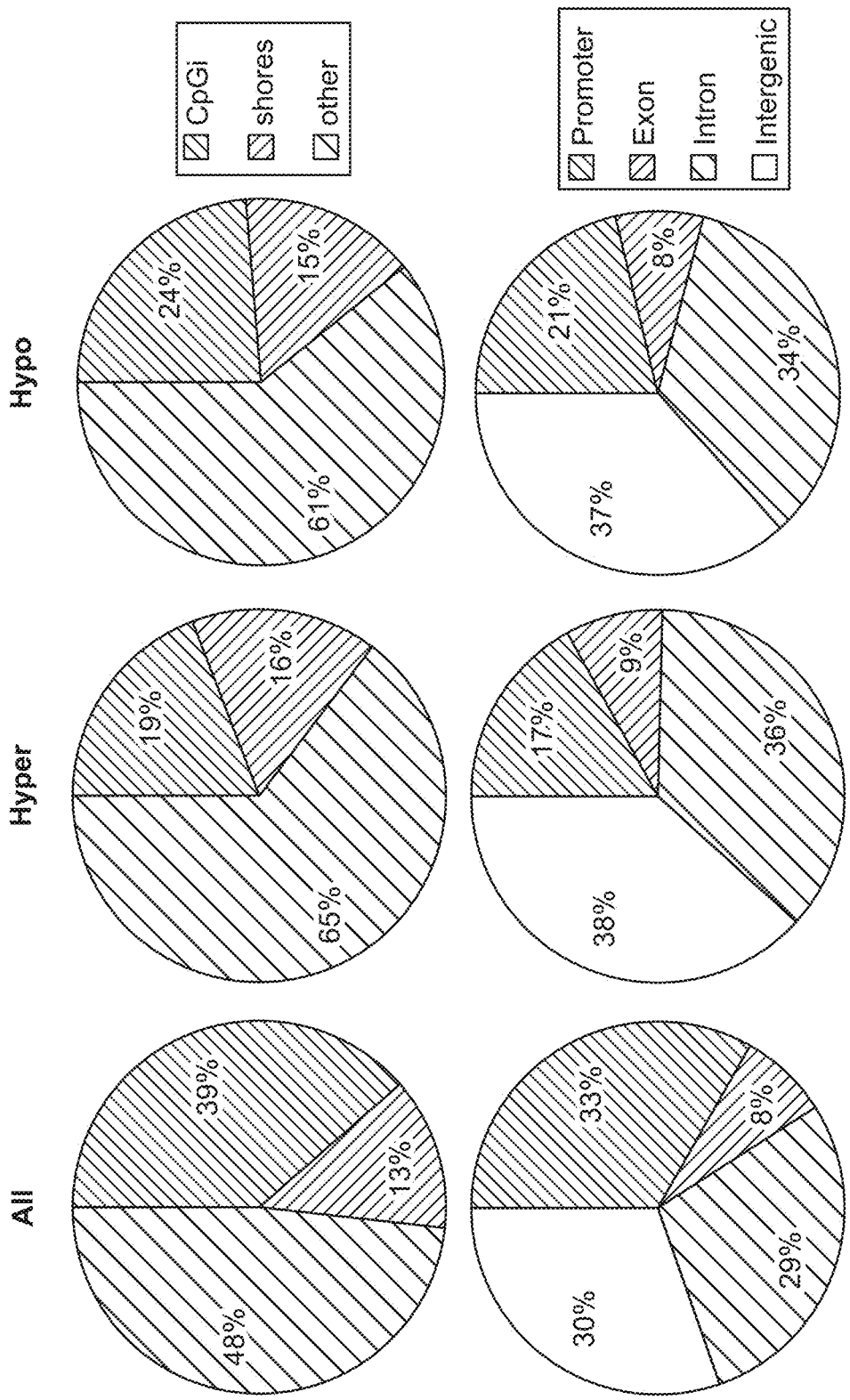
FIG. 16 shows distribution of differentially methylated CpG sites in human genome in a graphic depiction of the distribution of CpG sites over the entire genome that are differentially methylated in cells transfected with miR-155-5p versus a random 23-mer oligo.

The CpG density of non-overlapped 10 kb differentially methylated tiles was calculated. The density of tiles at a particular CpG density was plotted against the corresponding numbers of CpG sites per 10 kb (FIG. 14). The peak of density curve appeared at 78.3, 106.6 and 223.1 CpG sites per 10 kb in the groups containing all of the tiles analyzed, significantly hypermethylated tiles and significantly hypomethylated tiles, respectively. And this indicates that miR-155-5p mediated CpG demethylation preferentially occurs in CpG dense regions in the genome. Indeed, by comparing at the distribution of differentially methylated sites, we found that hypomethylated sites are more enriched in CpG islands than the hypermethylated sites, but most of the hypomethylated sites (60.8%) are still located in non-CpG islands or CpG island shore (±2000 bp) regions (FIG. 16, upper panel). And hypomethylated sites are also more enriched in promoter regions than hypermethylated sites (FIG. 16, lower panel). Here we conclude that miR-155-5p mediated genome-wide demethylation shows preference on medium-to-low level methylated CpG dense regions.

Figure 15:
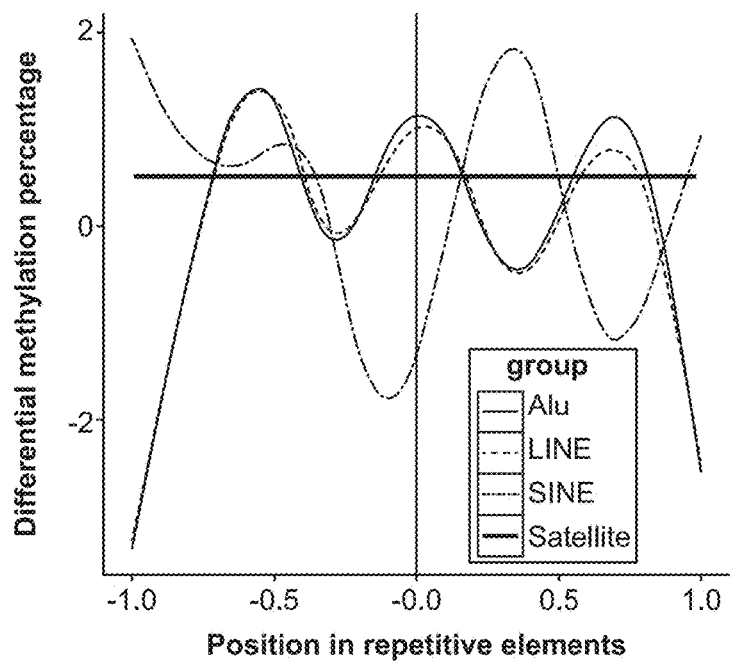
FIG. 15 shows a genome wide CPG methylation analysis using RRBS in a graphical depiction of the differential methylation of CpG motifs in Alu, LINE, SINE and satellite elements, by position within those elements, in cells transfected with mir-155-5p versus a random 23-mer oligo.

The methylation of repetitive elements in genome is prone to alter upon DNMTs are targeted in the cells (Deplus, et al., (2014)). We checked the methylation level of Alu, SINE, LINE and Satellite elements. Differentially methylated CpG sites were assigned to repetitive elements and the average differential methylation level at relative positions of repetitive elements was plotted. The border of SINE and Alu elements and the center of LINE elements showed hypomethylation, while Satellite elements showed hypermethylation (FIG. 15).

Example 10: Comparison Between Inhibitory RNA and a Clinical Drug (5-Azacytidine) on Mammalian Gene Expression Exogenous miR-155-5p causes significant DNA hypomethylation similar to 5-azacytidine drug in mammalian genome. Since miR-155-5p alters the methylation in CpG islands, we identified its influence on gene expression by RNA sequencing and transcriptome analysis. Paired-end sequencing reads were mapped to the UCSC human transcriptome (released Mar. 6, 2013) and unmapped reads were mapped to hg19 using Tophat (v2.0.11). FPKM (fragments per kilobase per million sequenced reads) values of known RNAs were calculated using Cuffdiff. With a threshold of 10% change in FPKM, 4311 RNAs were found to be upregulated in the miR-155-5p treated cells versus random oligo, R23 treated cells; while 3468 RNAs were down-regulated (FIG. 17). We also performed an identical transcriptome analysis between a well-recognized demethylation drug 5-azacytidine (AZC) versus untreated (no drug, ND) cells. The up and down regulated numbers of RNAs were 8818 and 6204 respectively with a ratio between upregulated vs. down regulated RNAs being similar to miR-155-5P and R23 (FIG. 18). We determined that about half the upregulated RNA and about one third of the down regulated RNAs were common between miR-155-5p and AZC in miR-155-5p transfected and 5-azacytidine treated cells. This demonstrates a common activation and repression pathways (FIGS. 19 and 20). Thus a subtle aberrant DNA methylation change by miR-155-5p activates pathways similar to demethylating drug AZC.

Figure 21:
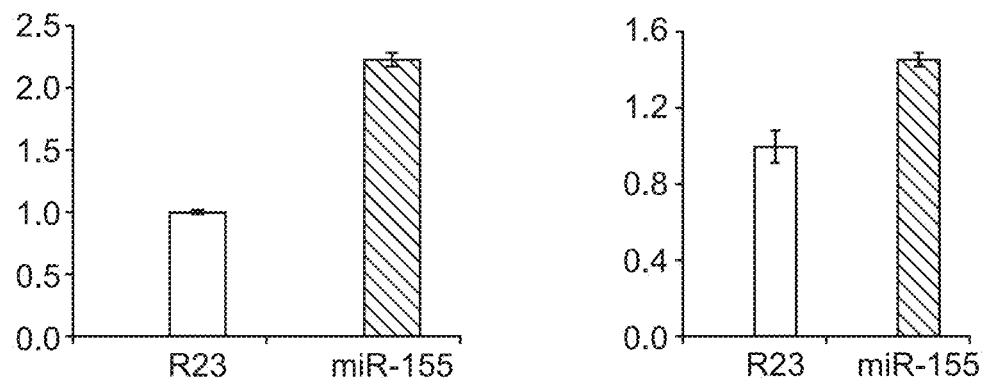
FIG. 21 shows CpG island hypomethylation resulted in increased gene expression in a graphical depiction of the levels of expression of the HRH2 and CASD1 genes, as measured by quantitative PCR, in cells transfected with miR-155-5p or with a random 23-mer oligo.

Example 11: Effect of microRNAs on Demethylation and Subsequent Gene Expression Genes with miR-155-5p induced promoter hypomethylation also show increased gene expression. To determine if microRNA mediated DNA methylation alteration affects the expression of corresponding genes, we investigated the expression levels of two of the genes with hypomethylated promoter regions, namely HRH2 and CASD1, by quantitative PCR assay. RNA was extracted from HCT 116 cells transfected with miRNA and 1 µg total RNA was reversed transcribed using the ProtoScript® II Reverse Transcriptase (New England Biolabs, Ipswich, Mass.). qPCR was carried out using the iQ™ SYBR® Green Supermix (Bio-Rad, Hercules, Calif.). Relative expression of genes was calculated using the 2-ΔΔCt method with GAPDH as a control. Primers used for qPCR analysis were HRH2_F, CCAGGCAACAGGAAGAGAAA; HRH2_R, TCATAATTCCTGGCATGTGG; CASD1_F, TCTGGCATTTTGGCTTACTG; CASD1_R, TCCATCTGAACCACCATTCA; GAPDH_F, GCCAAAAGGGTCATCATCTC; GAPDH_R, TGAGTCCTTCCACGATACCA. Both of the genes showed elevated expression levels (FIG. 21), consistent with miR- 155-5p not merely inducing hypomethylation, but increasing expression of the associated genes.

Example 12: MicroRNAs Co-Immunoprecipitate with DNMT in HCT-116 Cells

Figure 22:
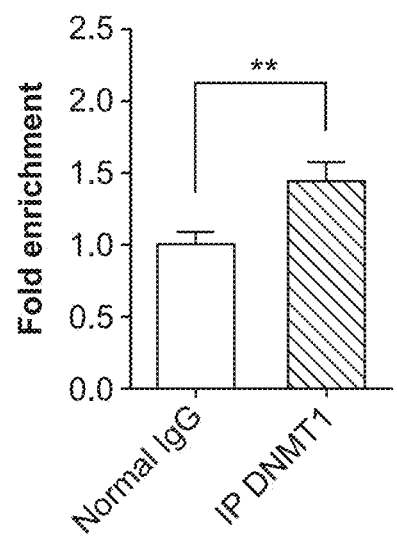
FIG. 22 shows that DNMT1 binds miR-155-5p in vivo in a graphical depiction of the relative amounts of miR-155-5p recovered from immunoprecipitations from cells when using an antibody to DNMT1 ("IP DNMT1") or a control antibody ("Normal IgG").

DNMT1 binds miR-155-5p in vivo. To confirm that the genome-wide hypomethylation was caused by the inhibition of DNMT1 by miR-155-5p, qPCR assay was performed on DNMT1-immunoprecipitated RNA. In brief, DNMT1 was immunoprecipitated from HCT-116 cell line with an ectopic plasmid integrated into the genome overexpressing miR-155-5p using DNMT1 N-16 antibody (Santa Cruz Biotechnology, Dallas, Tex.) or a normal IgG control. Then the bound RNA was extracted from immunoprecipitated DNMT1 and miR-155-5p was quantified using TaqMan® small RNA qPCR assay (Life Technologies, Grand Island, N.Y.). As shown in FIG. 22, the amount of miR-155-5p in the DNMT1 pull-down experiment is about 1.5-fold of that obtained using normal IgG control, indicating that DNMT1 binds miR-155-5p in the cells. The increased amount of miR-155-5p is statistically significant, with a p-value less than or equal to 0.001.

What is claimed:

1. A method of inhibiting DNA methylation by a DNA methyltransferase (DNMT), the method comprising:
   (a) contacting the DNMT with an RNA that has a modified backbone, the RNA having the sequence of SEQ ID NO: 4; and
   (b) inhibiting DNA methylation by the DNMT.

2. The method of claim 1, wherein the DNMT has a catalytic region that has an amino acid sequence that is at least 90% identical to amino acids 1081-1408 of human DNMT1 (SEQ ID NO:21).

3. The method of claim 2, wherein the catalytic region of the DNMT has an amino acid sequence that is at least 95% identical to amino acids 1081-1408 of human DNMT1 (SEQ ID NO:21).

4. The method of claim 3, wherein the catalytic region of the DNMT has an amino acid sequence that is identical to amino acids 1081-1408 of human DNMT1 (SEQ ID NO:21).

5. A method of inhibiting DNA methylation by a DNA methyltransferase (DNMT), the method comprising:
   (a) directly contacting the DNMT with an RNA that has a modified backbone, the RNA having an nucleotide sequence selected from the group consisting of SEQ ID NOS 4, 5 and 27; and
   (b) inhibiting DNA methylation by the DNMT.

* * * * *

SEQUENCE LISTING

```
<160> NUMBER OF SEQ ID NOS: 40

<210> SEQ ID NO 1
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1
ccgggacgca ggcggcguca ggc                                            23

<210> SEQ ID NO 2
<211> LENGTH: 23
<212> TYPE: RNA
<213> ORGANISM: Artificial Sequence
<220> FEATURE:
<223> OTHER INFORMATION: Synthetic construct

<400> SEQUENCE: 2
ccgggaagca ggcggcguca ggc                                            23

<210> SEQ ID NO 3
<211> LENGTH: 23
<212> TYPE: RNA
<213> ORGANISM: Artificial Sequence
<220> FEATURE:
<223> OTHER INFORMATION: Synthetic construct

<400> SEQUENCE: 3
gccaguggcg aggggcggcg cgg                                            23

<210> SEQ ID NO 4
<211> LENGTH: 23
<212> TYPE: RNA
<213> ORGANISM: Artificial Sequence
<220> FEATURE:
<223> OTHER INFORMATION: Synthetic construct

<400> SEQUENCE: 4
gacaguggag aggggcggag cgg                                            23

<210> SEQ ID NO 5
<211> LENGTH: 23
<212> TYPE: RNA
<213> ORGANISM: Artificial Sequence
<220> FEATURE:
<223> OTHER INFORMATION: Synthetic construct

<400> SEQUENCE: 5
uuaaugcuaa ucgugauagg ggu                                            23
```

```
<210> SEQ ID NO 6
<211> LENGTH: 23
<212> TYPE: RNA
<213> ORGANISM: Artificial Sequence
<220> FEATURE:
<223> OTHER INFORMATION: Synthetic construct

<400> SEQUENCE: 6
uuaaugcuaa ucgugauagg ggu                                          23

<210> SEQ ID NO 7
<211> LENGTH: 23
<212> TYPE: RNA
<213> ORGANISM: Artificial Sequence
<220> FEATURE:
<223> OTHER INFORMATION: Synthetic construct

<400> SEQUENCE: 7
uuaaugcuaa ucgugauagg ggu                                          23

<210> SEQ ID NO 8
<211> LENGTH: 23
<212> TYPE: RNA
<213> ORGANISM: Artificial Sequence
<220> FEATURE:
<223> OTHER INFORMATION: Synthetic construct

<400> SEQUENCE: 8
uuaaugcuaa ucgugauagg ggu                                          23

<210> SEQ ID NO 9
<211> LENGTH: 23
<212> TYPE: RNA
<213> ORGANISM: Artificial Sequence
<220> FEATURE:
<223> OTHER INFORMATION: Synthetic construct

<400> SEQUENCE: 9
uuaaugcuaa ucgugauagg ggu                                          23

<210> SEQ ID NO 10
<211> LENGTH: 23
<212> TYPE: RNA
<213> ORGANISM: Artificial Sequence
<220> FEATURE:
<223> OTHER INFORMATION: Synthetic construct

<400> SEQUENCE: 10
uuaaugcuaa ucgugauagg ggu                                          23

<210> SEQ ID NO 11
<211> LENGTH: 23
<212> TYPE: RNA
<213> ORGANISM: Artificial Sequence
<220> FEATURE:
<223> OTHER INFORMATION: Synthetic construct

<400> SEQUENCE: 11
uuaaugcuaa ucgugauagg ggu                                          23

<210> SEQ ID NO 12
<211> LENGTH: 23
<212> TYPE: RNA
<213> ORGANISM: Artificial Sequence
<220> FEATURE:
<223> OTHER INFORMATION: Synthetic construct
```

```
<400> SEQUENCE: 12
uuaaugcuaa ucgugauagg ggu                                              23

<210> SEQ ID NO 13
<211> LENGTH: 23
<212> TYPE: RNA
<213> ORGANISM: Artificial Sequence
<220> FEATURE:
<223> OTHER INFORMATION: Synthetic construct

<400> SEQUENCE: 13
uuaaugcuaa ucgugauagg ggu                                              23

<210> SEQ ID NO 14
<211> LENGTH: 23
<212> TYPE: RNA
<213> ORGANISM: Artificial Sequence
<220> FEATURE:
<223> OTHER INFORMATION: Synthetic construct

<400> SEQUENCE: 14
uuaaugcuaa ucgugauagg ggu                                              23

<210> SEQ ID NO 15
<211> LENGTH: 23
<212> TYPE: RNA
<213> ORGANISM: Artificial Sequence
<220> FEATURE:
<223> OTHER INFORMATION: Synthetic construct

<400> SEQUENCE: 15
uuaaugcuaa ucgugauagg ggu                                              23

<210> SEQ ID NO 16
<211> LENGTH: 23
<212> TYPE: RNA
<213> ORGANISM: Artificial Sequence
<220> FEATURE:
<223> OTHER INFORMATION: Synthetic construct

<400> SEQUENCE: 16
uuaaugcuaa ucgugauagg ggu                                              23

<210> SEQ ID NO 17
<211> LENGTH: 23
<212> TYPE: RNA
<213> ORGANISM: Artificial Sequence
<220> FEATURE:
<223> OTHER INFORMATION: Synthetic construct

<400> SEQUENCE: 17
uuaaugcuaa ucgugauagg ggu                                              23

<210> SEQ ID NO 18
<211> LENGTH: 23
<212> TYPE: RNA
<213> ORGANISM: Artificial Sequence
<220> FEATURE:
<223> OTHER INFORMATION: Synthetic construct

<400> SEQUENCE: 18
uuaaugcuaa ucgugauagg ggu                                              23

<210> SEQ ID NO 19
<211> LENGTH: 12
```

```
<212> TYPE: RNA
<213> ORGANISM: Artificial Sequence
<220> FEATURE:
<223> OTHER INFORMATION: Synthetic construct

<400> SEQUENCE: 19
uuaggguuag gg                                                          12

<210> SEQ ID NO 20
<211> LENGTH: 12
<212> TYPE: RNA
<213> ORGANISM: Artificial Sequence
<220> FEATURE:
<223> OTHER INFORMATION: Synthetic construct

<400> SEQUENCE: 20
auggggtggg gu                                                          12

<210> SEQ ID NO 21
<211> LENGTH: 1616
<212> TYPE: PRT
<213> ORGANISM: Homo sapiens

<400> SEQUENCE: 21
```

```
Met Pro Ala Arg Thr Ala Pro Ala Arg Val Pro Thr Leu Ala Val Pro
 1               5                  10                  15

Ala Ile Ser Leu Pro Asp Asp Val Arg Arg Arg Leu Lys Asp Leu Glu
            20                  25                  30

Arg Asp Ser Leu Thr Glu Lys Glu Cys Val Lys Glu Lys Leu Asn Leu
        35                  40                  45

Leu His Glu Phe Leu Gln Thr Glu Ile Lys Asn Gln Leu Cys Asp Leu
    50                  55                  60

Glu Thr Lys Leu Arg Lys Glu Glu Leu Ser Glu Gly Tyr Leu Ala
65                  70                  75                  80

Lys Val Lys Ser Leu Leu Asn Lys Asp Leu Ser Leu Glu Asn Gly Ala
                85                  90                  95

His Ala Tyr Asn Arg Glu Val Asn Gly Arg Leu Glu Asn Gly Asn Gln
            100                 105                 110

Ala Arg Ser Glu Ala Arg Arg Val Gly Met Ala Asp Ala Asn Ser Pro
        115                 120                 125

Pro Lys Pro Leu Ser Lys Pro Arg Thr Pro Arg Arg Ser Lys Ser Asp
    130                 135                 140

Gly Glu Ala Lys Pro Glu Pro Ser Pro Ser Pro Arg Ile Thr Arg Lys
145                 150                 155                 160

Ser Thr Arg Gln Thr Thr Ile Thr Ser His Phe Ala Lys Gly Pro Ala
                165                 170                 175

Lys Arg Lys Pro Gln Glu Glu Ser Glu Arg Ala Lys Ser Asp Glu Ser
            180                 185                 190

Ile Lys Glu Glu Asp Lys Asp Gln Asp Glu Lys Arg Arg Arg Val Thr
        195                 200                 205

Ser Arg Glu Arg Val Ala Arg Pro Leu Pro Ala Glu Glu Pro Glu Arg
    210                 215                 220

Ala Lys Ser Gly Thr Arg Thr Glu Lys Glu Glu Glu Arg Asp Glu Lys
225                 230                 235                 240

Glu Glu Lys Arg Leu Arg Ser Gln Thr Lys Glu Pro Thr Pro Lys Gln
                245                 250                 255

Lys Leu Lys Glu Glu Pro Asp Arg Glu Ala Arg Ala Gly Val Gln Ala
            260                 265                 270
```

```
Asp Glu Asp Glu Asp Gly Asp Glu Lys Asp Glu Lys Lys His Arg Ser
        275                 280                 285

Gln Pro Lys Asp Leu Ala Ala Lys Arg Arg Pro Glu Lys Glu Pro
290                 295                 300

Glu Lys Val Asn Pro Gln Ile Ser Asp Glu Lys Asp Glu Asp Glu Lys
305                 310                 315                 320

Glu Glu Lys Arg Arg Lys Thr Thr Pro Lys Glu Pro Thr Glu Lys Lys
            325                 330                 335

Met Ala Arg Ala Lys Thr Val Met Asn Ser Lys Thr His Pro Pro Lys
                340                 345                 350

Cys Ile Gln Cys Gly Gln Tyr Leu Asp Asp Pro Asp Leu Lys Tyr Gly
            355                 360                 365

Gln His Pro Pro Asp Ala Val Asp Glu Pro Gln Met Leu Thr Asn Glu
        370                 375                 380

Lys Leu Ser Ile Phe Asp Ala Asn Glu Ser Gly Phe Glu Ser Tyr Glu
385                 390                 395                 400

Ala Leu Pro Gln His Lys Leu Thr Cys Phe Ser Val Tyr Cys Lys His
                405                 410                 415

Gly His Leu Cys Pro Ile Asp Thr Gly Leu Ile Glu Lys Asn Ile Glu
            420                 425                 430

Leu Phe Phe Ser Gly Ser Ala Lys Pro Ile Tyr Asp Asp Asp Pro Ser
        435                 440                 445

Leu Glu Gly Gly Val Asn Gly Lys Asn Leu Gly Pro Ile Asn Glu Trp
450                 455                 460

Trp Ile Thr Gly Phe Asp Gly Gly Glu Lys Ala Leu Ile Gly Phe Ser
465                 470                 475                 480

Thr Ser Phe Ala Glu Tyr Ile Leu Met Asp Pro Ser Pro Glu Tyr Ala
                485                 490                 495

Pro Ile Phe Gly Leu Met Gln Glu Lys Ile Tyr Ile Ser Lys Ile Val
            500                 505                 510

Val Glu Phe Leu Gln Ser Asn Ser Asp Ser Thr Tyr Glu Asp Leu Ile
        515                 520                 525

Asn Lys Ile Glu Thr Thr Val Pro Pro Ser Gly Leu Asn Leu Asn Arg
    530                 535                 540

Phe Thr Glu Asp Ser Leu Leu Arg His Ala Gln Phe Val Val Glu Gln
545                 550                 555                 560

Val Glu Ser Tyr Asp Glu Ala Gly Asp Ser Asp Glu Gln Pro Ile Phe
                565                 570                 575

Leu Thr Pro Cys Met Arg Asp Leu Ile Lys Leu Ala Gly Val Thr Leu
            580                 585                 590

Gly Gln Arg Arg Ala Gln Ala Arg Arg Gln Thr Ile Arg His Ser Thr
        595                 600                 605

Arg Glu Lys Asp Arg Gly Pro Thr Lys Ala Thr Thr Thr Lys Leu Val
610                 615                 620

Tyr Gln Ile Phe Asp Thr Phe Phe Ala Glu Gln Ile Glu Lys Asp Asp
625                 630                 635                 640

Arg Glu Asp Lys Glu Asn Ala Phe Lys Arg Arg Arg Cys Gly Val Cys
                645                 650                 655

Glu Val Cys Gln Gln Pro Glu Cys Gly Lys Cys Lys Ala Cys Lys Asp
            660                 665                 670

Met Val Lys Phe Gly Gly Ser Gly Arg Ser Lys Gln Ala Cys Gln Glu
            675                 680                 685
```

-continued

```
Arg Arg Cys Pro Asn Met Ala Met Lys Glu Ala Asp Asp Glu Glu
690             695                 700

Val Asp Asp Asn Ile Pro Glu Met Pro Ser Pro Lys Lys Met His Gln
705                 710                 715                 720

Gly Lys Lys Lys Lys Gln Asn Lys Asn Arg Ile Ser Trp Val Gly Glu
        725                 730                 735

Ala Val Lys Thr Asp Gly Lys Lys Ser Tyr Tyr Lys Lys Val Cys Ile
            740                 745                 750

Asp Ala Glu Thr Leu Glu Val Gly Asp Cys Val Ser Val Ile Pro Asp
        755                 760                 765

Asp Ser Ser Lys Pro Leu Tyr Leu Ala Arg Val Thr Ala Leu Trp Glu
770                 775                 780

Asp Ser Ser Asn Gly Gln Met Phe His Ala His Trp Phe Cys Ala Gly
785                 790                 795                 800

Thr Asp Thr Val Leu Gly Ala Thr Ser Asp Pro Leu Glu Leu Phe Leu
            805                 810                 815

Val Asp Glu Cys Glu Asp Met Gln Leu Ser Tyr Ile His Ser Lys Val
            820                 825                 830

Lys Val Ile Tyr Lys Ala Pro Ser Glu Asn Trp Ala Met Glu Gly Gly
            835                 840                 845

Met Asp Pro Glu Ser Leu Leu Glu Gly Asp Asp Gly Lys Thr Tyr Phe
850                 855                 860

Tyr Gln Leu Trp Tyr Asp Gln Asp Tyr Ala Arg Phe Glu Ser Pro Pro
865                 870                 875                 880

Lys Thr Gln Pro Thr Glu Asp Asn Lys Phe Lys Phe Cys Val Ser Cys
                885                 890                 895

Ala Arg Leu Ala Glu Met Arg Gln Lys Glu Ile Pro Arg Val Leu Glu
            900                 905                 910

Gln Leu Glu Asp Leu Asp Ser Arg Val Leu Tyr Tyr Ser Ala Thr Lys
        915                 920                 925

Asn Gly Ile Leu Tyr Arg Val Gly Asp Gly Val Tyr Leu Pro Pro Glu
        930                 935                 940

Ala Phe Thr Phe Asn Ile Lys Leu Ser Ser Pro Val Lys Arg Pro Arg
945                 950                 955                 960

Lys Glu Pro Val Asp Glu Asp Leu Tyr Pro Glu His Tyr Arg Lys Tyr
                965                 970                 975

Ser Asp Tyr Ile Lys Gly Ser Asn Leu Asp Ala Pro Glu Pro Tyr Arg
            980                 985                 990

Ile Gly Arg Ile Lys Glu Ile Phe Cys Pro Lys Lys Ser Asn Gly Arg
        995                 1000                1005

Pro Asn Glu Thr Asp Ile Lys Ile Arg Val Asn Lys Phe Tyr Arg
    1010                1015                1020

Pro Glu Asn Thr His Lys Ser Thr Pro Ala Ser Tyr His Ala Asp
    1025                1030                1035

Ile Asn Leu Leu Tyr Trp Ser Asp Glu Glu Ala Val Val Asp Phe
    1040                1045                1050

Lys Ala Val Gln Gly Arg Cys Thr Val Glu Tyr Gly Glu Asp Leu
    1055                1060                1065

Pro Glu Cys Val Gln Val Tyr Ser Met Gly Gly Pro Asn Arg Phe
    1070                1075                1080

Tyr Phe Leu Glu Ala Tyr Asn Ala Lys Ser Lys Ser Phe Glu Asp
    1085                1090                1095

Pro Pro Asn His Ala Arg Ser Pro Gly Asn Lys Gly Lys Gly Lys
```

-continued

|  | 1100 |  |  | 1105 |  |  | 1110 |  |  |
| Gly | Lys | Gly | Lys | Gly | Lys | Pro | Lys | Ser | Gln | Ala | Cys | Glu | Pro | Ser |
|  | 1115 |  |  |  | 1120 |  |  |  | 1125 |  |  |  |  |  |
| Glu | Pro | Glu | Ile | Glu | Ile | Lys | Leu | Pro | Lys | Leu | Arg | Thr | Leu | Asp |
|  | 1130 |  |  |  | 1135 |  |  |  | 1140 |  |  |  |  |  |
| Val | Phe | Ser | Gly | Cys | Gly | Gly | Leu | Ser | Glu | Gly | Phe | His | Gln | Ala |
|  | 1145 |  |  |  | 1150 |  |  |  | 1155 |  |  |  |  |  |
| Gly | Ile | Ser | Asp | Thr | Leu | Trp | Ala | Ile | Glu | Met | Trp | Asp | Pro | Ala |
|  | 1160 |  |  |  | 1165 |  |  |  | 1170 |  |  |  |  |  |
| Ala | Gln | Ala | Phe | Arg | Leu | Asn | Asn | Pro | Gly | Ser | Thr | Val | Phe | Thr |
|  | 1175 |  |  |  | 1180 |  |  |  | 1185 |  |  |  |  |  |
| Glu | Asp | Cys | Asn | Ile | Leu | Leu | Lys | Leu | Val | Met | Ala | Gly | Glu | Thr |
|  | 1190 |  |  |  | 1195 |  |  |  | 1200 |  |  |  |  |  |
| Thr | Asn | Ser | Arg | Gly | Gln | Arg | Leu | Pro | Gln | Lys | Gly | Asp | Val | Glu |
|  | 1205 |  |  |  | 1210 |  |  |  | 1215 |  |  |  |  |  |
| Met | Leu | Cys | Gly | Gly | Pro | Pro | Cys | Gln | Gly | Phe | Ser | Gly | Met | Asn |
|  | 1220 |  |  |  | 1225 |  |  |  | 1230 |  |  |  |  |  |
| Arg | Phe | Asn | Ser | Arg | Thr | Tyr | Ser | Lys | Phe | Lys | Asn | Ser | Leu | Val |
|  | 1235 |  |  |  | 1240 |  |  |  | 1245 |  |  |  |  |  |
| Val | Ser | Phe | Leu | Ser | Tyr | Cys | Asp | Tyr | Tyr | Arg | Pro | Arg | Phe | Phe |
|  | 1250 |  |  |  | 1255 |  |  |  | 1260 |  |  |  |  |  |
| Leu | Leu | Glu | Asn | Val | Arg | Asn | Phe | Val | Ser | Phe | Lys | Arg | Ser | Met |
|  | 1265 |  |  |  | 1270 |  |  |  | 1275 |  |  |  |  |  |
| Val | Leu | Lys | Leu | Thr | Leu | Arg | Cys | Leu | Val | Arg | Met | Gly | Tyr | Gln |
|  | 1280 |  |  |  | 1285 |  |  |  | 1290 |  |  |  |  |  |
| Cys | Thr | Phe | Gly | Val | Leu | Gln | Ala | Gly | Gln | Tyr | Gly | Val | Ala | Gln |
|  | 1295 |  |  |  | 1300 |  |  |  | 1305 |  |  |  |  |  |
| Thr | Arg | Arg | Arg | Ala | Ile | Ile | Leu | Ala | Ala | Ala | Pro | Gly | Glu | Lys |
|  | 1310 |  |  |  | 1315 |  |  |  | 1320 |  |  |  |  |  |
| Leu | Pro | Leu | Phe | Pro | Glu | Pro | Leu | His | Val | Phe | Ala | Pro | Arg | Ala |
|  | 1325 |  |  |  | 1330 |  |  |  | 1335 |  |  |  |  |  |
| Cys | Gln | Leu | Ser | Val | Val | Val | Asp | Asp | Lys | Lys | Phe | Val | Ser | Asn |
|  | 1340 |  |  |  | 1345 |  |  |  | 1350 |  |  |  |  |  |
| Ile | Thr | Arg | Leu | Ser | Ser | Gly | Pro | Phe | Arg | Thr | Ile | Thr | Val | Arg |
|  | 1355 |  |  |  | 1360 |  |  |  | 1365 |  |  |  |  |  |
| Asp | Thr | Met | Ser | Asp | Leu | Pro | Glu | Val | Arg | Asn | Gly | Ala | Ser | Ala |
|  | 1370 |  |  |  | 1375 |  |  |  | 1380 |  |  |  |  |  |
| Leu | Glu | Ile | Ser | Tyr | Asn | Gly | Glu | Pro | Gln | Ser | Trp | Phe | Gln | Arg |
|  | 1385 |  |  |  | 1390 |  |  |  | 1395 |  |  |  |  |  |
| Gln | Leu | Arg | Gly | Ala | Gln | Tyr | Gln | Pro | Ile | Leu | Arg | Asp | His | Ile |
|  | 1400 |  |  |  | 1405 |  |  |  | 1410 |  |  |  |  |  |
| Cys | Lys | Asp | Met | Ser | Ala | Leu | Val | Ala | Ala | Arg | Met | Arg | His | Ile |
|  | 1415 |  |  |  | 1420 |  |  |  | 1425 |  |  |  |  |  |
| Pro | Leu | Ala | Pro | Gly | Ser | Asp | Trp | Arg | Asp | Leu | Pro | Asn | Ile | Glu |
|  | 1430 |  |  |  | 1435 |  |  |  | 1440 |  |  |  |  |  |
| Val | Arg | Leu | Ser | Asp | Gly | Thr | Met | Ala | Arg | Lys | Leu | Arg | Tyr | Thr |
|  | 1445 |  |  |  | 1450 |  |  |  | 1455 |  |  |  |  |  |
| His | His | Asp | Arg | Lys | Asn | Gly | Arg | Ser | Ser | Ser | Gly | Ala | Leu | Arg |
|  | 1460 |  |  |  | 1465 |  |  |  | 1470 |  |  |  |  |  |
| Gly | Val | Cys | Ser | Cys | Val | Glu | Ala | Gly | Lys | Ala | Cys | Asp | Pro | Ala |
|  | 1475 |  |  |  | 1480 |  |  |  | 1485 |  |  |  |  |  |
| Ala | Arg | Gln | Phe | Asn | Thr | Leu | Ile | Pro | Trp | Cys | Leu | Pro | His | Thr |
|  | 1490 |  |  |  | 1495 |  |  |  | 1500 |  |  |  |  |  |

-continued

```
Gly Asn Arg His Asn His Trp Ala Gly Leu Tyr Gly Arg Leu Glu
    1505                1510                1515

Trp Asp Gly Phe Phe Ser Thr Thr Val Thr Asn Pro Glu Pro Met
1520                1525                1530

Gly Lys Gln Gly Arg Val Leu His Pro Glu Gln His Arg Val Val
    1535                1540                1545

Ser Val Arg Glu Cys Ala Arg Ser Gln Gly Phe Pro Asp Thr Tyr
1550                1555                1560

Arg Leu Phe Gly Asn Ile Leu Asp Lys His Arg Gln Val Gly Asn
    1565                1570                1575

Ala Val Pro Pro Pro Leu Ala Lys Ala Ile Gly Leu Glu Ile Lys
1580                1585                1590

Leu Cys Met Leu Ala Lys Ala Arg Glu Ser Ala Ser Ala Lys Ile
    1595                1600                1605

Lys Glu Glu Glu Ala Ala Lys Asp
1610                1615

<210> SEQ ID NO 22
<211> LENGTH: 23
<212> TYPE: RNA
<213> ORGANISM: Artificial Sequence
<220> FEATURE:
<223> OTHER INFORMATION: Synthetic construct

<400> SEQUENCE: 22
ucuuugguua ucuagcugua uga                                              23

<210> SEQ ID NO 23
<211> LENGTH: 23
<212> TYPE: RNA
<213> ORGANISM: Artificial Sequence
<220> FEATURE:
<223> OTHER INFORMATION: Synthetic construct

<400> SEQUENCE: 23
caaagugcuu acagugcagg uag                                              23

<210> SEQ ID NO 24
<211> LENGTH: 22
<212> TYPE: RNA
<213> ORGANISM: Artificial Sequence
<220> FEATURE:
<223> OTHER INFORMATION: Synthetic Construct

<400> SEQUENCE: 24
uagcuuauca gacugauguu ga                                               22

<210> SEQ ID NO 25
<211> LENGTH: 23
<212> TYPE: RNA
<213> ORGANISM: Artificial Sequence
<220> FEATURE:
<223> OTHER INFORMATION: Synthetic Construct

<400> SEQUENCE: 25
agguugggau cgguugcaau gcu                                              23

<210> SEQ ID NO 26
<211> LENGTH: 22
<212> TYPE: RNA
<213> ORGANISM: Artificial Sequence
<220> FEATURE:
```

<223> OTHER INFORMATION: Synthetic Construct

<400> SEQUENCE: 26
uauugcacuu gucccggccu gu                                        22

<210> SEQ ID NO 27
<211> LENGTH: 22
<212> TYPE: RNA
<213> ORGANISM: Artificial Sequence
<220> FEATURE:
<223> OTHER INFORMATION: Synthetic Construct

<400> SEQUENCE: 27
ucggauccgu cugagcuugg cu                                        22

<210> SEQ ID NO 28
<211> LENGTH: 22
<212> TYPE: RNA
<213> ORGANISM: Artificial Sequence
<220> FEATURE:
<223> OTHER INFORMATION: Synthetic Construct

<400> SEQUENCE: 28
auaaagcuag auaaccgaaa gu                                        22

<210> SEQ ID NO 29
<211> LENGTH: 22
<212> TYPE: RNA
<213> ORGANISM: Artificial Sequence
<220> FEATURE:
<223> OTHER INFORMATION: Synthetic Construct

<400> SEQUENCE: 29
uagcagcacg uaaauauugg cg                                        22

<210> SEQ ID NO 30
<211> LENGTH: 23
<212> TYPE: RNA
<213> ORGANISM: Artificial Sequence
<220> FEATURE:
<223> OTHER INFORMATION: Synthetic Construct

<400> SEQUENCE: 30
ugugcaaauc caugcaaaac uga                                       23

<210> SEQ ID NO 31
<211> LENGTH: 23
<212> TYPE: RNA
<213> ORGANISM: Artificial Sequence
<220> FEATURE:
<223> OTHER INFORMATION: Synthetic Construct

<400> SEQUENCE: 31
uaaagugcuu auagugcagg uag                                       23

<210> SEQ ID NO 32
<211> LENGTH: 23
<212> TYPE: RNA
<213> ORGANISM: Artificial Sequence
<220> FEATURE:
<223> OTHER INFORMATION: Synthetic Construct

<400> SEQUENCE: 32
guccaguuuu cccaggaauc ccu                                       23

```
<210> SEQ ID NO 33
<211> LENGTH: 22
<212> TYPE: RNA
<213> ORGANISM: Artificial Sequence
<220> FEATURE:
<223> OTHER INFORMATION: Synthetic Construct

<400> SEQUENCE: 33
ugagaacuga auuccauggg uu                                                22

<210> SEQ ID NO 34
<211> LENGTH: 22
<212> TYPE: RNA
<213> ORGANISM: Artificial Sequence
<220> FEATURE:
<223> OTHER INFORMATION: Synthetic Construct

<400> SEQUENCE: 34
acucaaaaug ggggcgcuuu cc                                                22

<210> SEQ ID NO 35
<211> LENGTH: 23
<212> TYPE: RNA
<213> ORGANISM: Artificial Sequence
<220> FEATURE:
<223> OTHER INFORMATION: Synthetic construct

<400> SEQUENCE: 35
aggacgugcg cggcggagag cgc                                               23

<210> SEQ ID NO 36
<211> LENGTH: 23
<212> TYPE: RNA
<213> ORGANISM: Artificial Sequence
<220> FEATURE:
<223> OTHER INFORMATION: Synthetic Construct

<400> SEQUENCE: 36
aguucgaugu cggggcucgg aau                                               23

<210> SEQ ID NO 37
<211> LENGTH: 23
<212> TYPE: RNA
<213> ORGANISM: Artificial Sequence
<220> FEATURE:
<223> OTHER INFORMATION: Synthetic Construct

<400> SEQUENCE: 37
aacgaguagg acgugcgcgg cgg                                               23

<210> SEQ ID NO 38
<211> LENGTH: 23
<212> TYPE: RNA
<213> ORGANISM: Artificial Sequence
<220> FEATURE:
<223> OTHER INFORMATION: Synthetic Construct

<400> SEQUENCE: 38
aaaagggaac gugagcuggg uuu                                               23

<210> SEQ ID NO 39
<211> LENGTH: 23
<212> TYPE: RNA
<213> ORGANISM: Artificial Sequence
<220> FEATURE:
<223> OTHER INFORMATION: Synthetic Construct
```

-continued

<400> SEQUENCE: 39
agcgaacaag uaccgugagg gaa                                                    23

<210> SEQ ID NO 40
<211> LENGTH: 23
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: N at position 1 may be A, C or U
<220> FEATURE:
<221> NAME/KEY: misc_feature
<222> LOCATION: (2)..(2)
<223> OTHER INFORMATION: N at position 2 may be A, G or U
<220> FEATURE:
<221> NAME/KEY: misc_feature
<222> LOCATION: (3)..(3)
<223> OTHER INFORMATION: N at position 3 may any nucleotide
<220> FEATURE:
<221> NAME/KEY: misc_feature
<222> LOCATION: (4)..(4)
<223> OTHER INFORMATION: N at position 4 may be A, G or U
<220> FEATURE:
<221> NAME/KEY: misc_feature
<222> LOCATION: (5)..(5)
<223> OTHER INFORMATION: N at position 5 may any nucleotide
<220> FEATURE:
<221> NAME/KEY: misc_feature
<222> LOCATION: (6)..(6)
<223> OTHER INFORMATION: N at position 6 may be A, G or U
<220> FEATURE:
<221> NAME/KEY: misc_feature
<222> LOCATION: (7)..(12)
<223> OTHER INFORMATION: N may be any nucleotide
<220> FEATURE:
<221> NAME/KEY: misc_feature
<222> LOCATION: (13)..(13)
<223> OTHER INFORMATION: N at position 13 may be G, A or C
<220> FEATURE:
<221> NAME/KEY: misc_feature
<222> LOCATION: (14)..(14)
<223> OTHER INFORMATION: N may any nucleotide
<220> FEATURE:
<221> NAME/KEY: misc_feature
<222> LOCATION: (15)..(15)
<223> OTHER INFORMATION: N at position 15 may be G or U
<220> FEATURE:
<221> NAME/KEY: misc_feature
<222> LOCATION: (16)..(17)
<223> OTHER INFORMATION: N may any nucleotide
<220> FEATURE:
<221> NAME/KEY: misc_feature
<222> LOCATION: (18)..(18)
<223> OTHER INFORMATION: N at position 18 may be A, C or G
<220> FEATURE:
<221> NAME/KEY: misc_feature
<222> LOCATION: (19)..(19)
<223> OTHER INFORMATION: N at position 18 may be A or G
<220> FEATURE:
<221> NAME/KEY: misc_feature
<222> LOCATION: (21)..(21)
<223> OTHER INFORMATION: N may any nucleotide
<220> FEATURE:
<221> NAME/KEY: misc_feature
<222> LOCATION: (22)..(22)
<223> OTHER INFORMATION: N at position 22 may be A, G or U
<220> FEATURE:

```
<221> NAME/KEY: misc_feature
<222> LOCATION: (23)..(23)
<223> OTHER INFORMATION: N may be any nucleotide

<400> SEQUENCE: 40
nnnnnnnnnn nnnnnnnnng nnn                                          23
```